US010087259B1

(12) United States Patent
Rudensky et al.

(10) Patent No.: US 10,087,259 B1
(45) Date of Patent: Oct. 2, 2018

(54) DEPLETING TUMOR-SPECIFIC TREGS

(71) Applicant: MEMORIAL SLOAN KETTERING CANCER CENTER, New York, NY (US)

(72) Inventors: Alexander Rudensky, New York, NY (US); George Plitas, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 0 days.

(21) Appl. No.: 14/698,600

(22) Filed: Apr. 28, 2015

Related U.S. Application Data

(60) Provisional application No. 61/985,329, filed on Apr. 28, 2014.

(51) Int. Cl.
*A61K 39/00* (2006.01)
*C07K 16/30* (2006.01)
*G01N 33/574* (2006.01)

(52) U.S. Cl.
CPC ... *C07K 16/3061* (2013.01); *G01N 33/57426* (2013.01); *A61K 2039/505* (2013.01); *C07K 2317/31* (2013.01); *G01N 2333/7158* (2013.01)

(58) Field of Classification Search
None
See application file for complete search history.

(56) References Cited

U.S. PATENT DOCUMENTS

| | | | |
|---|---|---|---|
| 4,816,567 A | | 3/1989 | Cabilly et al. |
| 5,078,998 A | | 1/1992 | Bevan et al. |
| 5,091,513 A | | 2/1992 | Huston et al. |
| 5,225,539 A | | 7/1993 | Winter |
| 5,585,089 A | | 12/1996 | Queen et al. |
| 5,693,761 A | | 12/1997 | Queen et al. |
| 5,693,762 A | | 12/1997 | Queen et al. |
| 5,869,619 A | | 2/1999 | Studnicka |
| 6,180,370 B1 | | 1/2001 | Queen et al. |
| 6,548,640 B1 | | 4/2003 | Winter |
| 6,881,557 B2 | | 4/2005 | Foote |
| 6,982,321 B2 | | 1/2006 | Winter |
| 7,241,444 B2 | * | 7/2007 | Goetsch .......... A61K 47/48392 424/130.1 |
| 2007/0009544 A1 | * | 1/2007 | Eisenberg .......... A61K 39/0008 424/185.1 |
| 2009/0214533 A1 | * | 8/2009 | Clynes ................. C07K 16/32 424/133.1 |
| 2015/0266959 A1 | * | 9/2015 | Vignali ................ A61K 31/713 424/174.1 |
| 2018/0038860 A1 | * | 2/2018 | Winqvist ............. G01N 33/566 |

OTHER PUBLICATIONS

Casset et al. A peptide mimetic of an anti-CD4 monoclonal antibody by rational design. Biochem Biophys Res Commun. Jul. 18, 2003;307(1):198-205.*
Chen et al. Selection and analysis of an optimized anti-VEGF antibody: crystal structure of an affinity-matured Fab in complex with antigen. J Mol Biol. Nov. 5, 1999;293(4):865-81.*
De Pascalis et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.*
Drakes ML, Stiff PJ. Harnessing immunosurveillance: current developments and future directions in cancer immunotherapy. Immunotargets Ther. Dec. 4, 2014;3:151-65.*
Holm et al. Functional mapping and single chain construction of the anti-cytokeratin 8 monoclonal antibody TS1. Mol Immunol. Feb. 2007;44(6):1075-84. Epub Sep. 20, 2006.*
Iellem et al. Unique chemotactic response profile and specific expression of chemokine receptors CCR4 and CCR8 by CD4(+)CD25(+) regulatory T cells. J Exp Med. Sep. 17, 2001;194(6):847-53.*
MacCallum et al. Antibody-antigen interactions: contact analysis and binding site topography. J Mol Biol. Oct. 11, 1996;262(5):732-45.*
Rudikoff et al. Single amino acid substitution altering antigen-binding specificity. Proc Natl Acad Sci U S A. Mar. 1982;79(6):1979-83.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Wu et al. Humanization of a murine monoclonal antibody by simultaneous optimization of framework and CDR residues. J Mol Biol. Nov. 19, 1999;294(1):151-62.*
Wang et al. PLoS One. 2012;7(1):e30793. doi: 10.1371/journal.pone.0030793.*
Hoelzinger et al., The Journal of Immunology 184 (2010) 6833-6842 (Year: 2010).*
Al-Shibli, K.I. et al., Prognostic effect of epithelial and stromal lymphocyte infiltration in non-small cell lung cancer, Clin. Cancer Res., 14(16):5220-5227 (2008).
Amedei, A. et al., Novel immunotherapeutic strategies of gastric cancer treatment, J. Biomed. Biotechnol., 2011:437348 (2011).
Balachandran, V.P., et al., Imatinib potentiates antitumor T cell responses in gastrointestinal stromal tumor through the inhibition of Ido, Nat. Med., 17(9):1094-100 (2011).
Barzaghi, F. et al., Immune dysregulation, polyendocrinopathy, enteropathy, x-linked syndrome: a paradigm of immunodeficiency with autoimmunity, Front. Immunol., 3:211 (2012).
Bates, G.J. et al., Quantification of regulatory T cells enables the identification of high-risk breast cancer patients and those at risk of late relapse, J. Clin. Oncol., 24(34):5373-80 (2006).
Bindea, G. et al., Spatiotemporal dynamics of intratumoral immune cells reveal the immune landscape in human cancer, Immunity, 39(4):782-95 (2013).
Bohling, S.D. and Allison, K.H., Immunosuppressive regulatory T cells are associated with aggressive breast cancer phenotypes: a potential therapeutic target, Mod. Pathol., 21(12):1527-32 (2008).

(Continued)

*Primary Examiner* — Daniel C Gamett
(74) *Attorney, Agent, or Firm* — Choate, Hall & Stewart, LLP; Brenda Herschbach Jarrell; Michael L. Vetter

(57) ABSTRACT

The present invention provides, among other things, methods and compositions for diagnosing and/or treating cancer by targeting CCR8. In particular, the present invention provides technologies for depleting Treg cells, and particularly tumor-infiltrating Treg cells.

6 Claims, 10 Drawing Sheets

(56) References Cited

OTHER PUBLICATIONS

Bos, P.D. et al., Transient regulatory T cell ablation deters oncogene-driven breast cancer and enhances radiotherapy, J. Exp. Med., 210(11):2435-66 (2013).
Brahmer, J.R. et al., Safety and activity of anti-PD-L1 antibody in patients with advanced cancer, N. Engl. J. Med., 366(26):2455-65 (2012).
Buckner, J.H., Mechanisms of impaired regulation by CD4(+)CD25(+)FOXP3(+) regulatory T cells in human autoimmune diseases, Nat. Rev. Immunol., 10(12):849-59 (2010).
Cancer Genome Atlas Network, Comprehensive molecular portraits of human breast tumours, Nature, 490(7418):61-70 (2012).
Casares, N. et al., A peptide inhibitor of FOXP3 impairs regulatory T cell activity and improves vaccine efficacy in mice, J. Immunol., 185(9):5150-9 (2010).
Cetin, K. et al., Survival by histologic subtype in stage IV nonsmall cell lung cancer based on data from the Surveillance, Epidemiology and End Results Program, Clin Epidemiol., 3:139-48 (2011).
Chaudhry, A. and Rudensky, A.Y., Control of inflammation by integration of environmental cues by regulatory T cells, J. Clin. Invest., 123(3):939-44 (2013).
Chaudhry, A. et al., CD4+ regulatory T cells control TH17 responses in a Stat3-dependent manner, Science, 326(5955):986-91 (2009).
Chen, C.A., et al., Metronomic chemotherapy enhances antitumor effects of cancer vaccine by depleting regulatory T lymphocytes and inhibiting tumor angiogenesis, Mol. Ther., 18(6):1233-43 (2010).
Chinen, T. and Rudensky, A.Y., The effects of commensal microbiota on immune cell subsets and inflammatory responses, Immunol. Rev., 245(1):45-55 (2012).
Chinen, T. et al., A critical role for regulatory T cell-mediated control of inflammation in the absence of commensal microbiota, J. Exp. Med., 207(11):2323-30 (2010).
Conforti, R. et al., Opposing effects of toll-like receptor (TLR3) signaling in tumors can be therapeutically uncoupled to optimize the anticancer efficacy of TLR3 ligands, Cancer Res., 70(2):490-500 (2010).
Curiel, T.J. et al., Specific recruitment of regulatory T cells in ovarian carcinoma fosters immune privilege and predicts reduced survival, Nat. Med. 10(9):942-9 (2004).
Deleeuw, R.J. et al., The prognostic value of FoxP3+ tumor-infiltrating lymphocytes in cancer: a critical review of the literature, Clin. Cancer Res., 18(11):3022-9 (2012).
Denardo, D.G. et al., CD4(+) T cells regulate pulmonary metastasis of mammary carcinomas by enhancing protumor properties of macrophages, Cancer Cell, 16(2):91-102 (2009).
Deng, B. et al., Intratumor hypoxia promotes immune tolerance by inducing regulatory T cells via TGF-β1 in gastric cancer, PLoS One, 8(5):e63777 (2013).
Dhamne, C. et al., Peripheral and thymic foxp3(+) regulatory T cells in search of origin, distinction, and function, Front. Immunol., 4:253 (2013).
Ducancel, F. And Muller, B.H., Molecular engineering of antibodies for therapeutic and diagnostic purposes, MAbs., 4(4):445-57 (2012).
Dunn, G.P. et al., The immunobiology of cancer immunosurveillance and immunoediting, Immunity, 21(2):137-48 (2004).
Ercolini, A.M. et al., Recruitment of latent pools of high-avidity CD8(+) T cells to the antitumor immune response, J. Exp. Med., 201(10):1591-602 (2005).
Fellmann, C. et al., An optimized microRNA backbone for effective single-copy RNAi, Cell Rep., 5(6):1704-13 (2013).
Fontenot, J.D. et al., Foxp3 programs the development and function of CD4+CD25+ regulatory T cells, Nat. Immunol., 4(4):330-6 (2003).
Formenti, S.C. and Demaria, S., Systemic effects of local radiotherapy, Lancet Oncol., 10(7):718-26 (2009).
Galon, J. et al., Type, density, and location of immune cells within human colorectal tumors predict clinical outcome, Science, 313(5795):1960-4 (2006).
Gerner, M.Y. et al., Histo-cytometry: a method for highly multiplex quantitative tissue imaging analysis applied to dendritic cell subset microanatomy in lymph nodes, Immunity, 37(2):364-76 (2012).
Gobert, M. et al., Regulatory T cells recruited through CCL22/CCR4 are selectively activated in lymphoid infiltrates surrounding primary breast tumors and lead to an adverse clinical outcome, Cancer Res., 69(5):2000-9 (2009).
Hiraoka, N. et al., Prevalence of FOXP3+ regulatory T cells increases during the progression of pancreatic ductal adenocarcinoma and its premalignant lesions, Clin. Cancer Res., 12(18):5423-34 (2006).
Hodi, F.S. et al., Improved survival with ipilimumab in patients with metastatic melanoma, N. Engl. J. Med., 363(8):711-23 (2010).
Hooper, L.V. et al., Interactions between the microbiota and the immune system, Science, 336(6086):1268-73 (2012).
Hori, S. et al., Control of regulatory T cell development by the transcription factor Foxp3, Science, 299(5609):1057-61 (2003).
Iida, S. et al., Nonfucosylated therapeutic IgG1 antibody can evade the inhibitory effect of serum immunoglobulin G on antibody-dependent cellular cytotoxicity through its high binding to FcgammaRIIIa, Clin. Cancer Res., 12(9):2879-87 (2006).
Islam, S.A. et al., Identification of human CCR8 as a CCL18 receptor, J. Exp. Med., 210(10):1889-98 (2013).
Islam, S.A. et al., Mouse CCL8, a CCR8 agonist, promotes atopic dermatitis by recruiting IL-5+ T(H)2 cells, Nat. Immunol., 12(2):167-77 (2011).
Josefowicz, S.Z. et al., Extrathymically generated regulatory T cells control mucosal TH2 inflammation, Nature, 482(7385):395-9 (2012).
Josefowicz, S.Z. et al., Regulatory T cells: mechanisms of differentiation and function, Annu. Rev. Immunol., 30:531-64 (2012).
Kantoff, P.W. et al., Sipuleucel-T immunotherapy for castration-resistant prostate cancer, N. Engl. J. Med., 363(5):411-22 (2010).
Kim, J. et al., Cutting edge: depletion of Foxp3+ cells leads to induction of autoimmunity by specific ablation of regulatory T cells in genetically targeted mice, J. Immunol., 183(12):7631-4 (2009).
Kim, J.M. et al., Regulatory T cells prevent catastrophic autoimmunity throughout the lifespan of mice, Nat. Immunol., 8(2):191-7 (2007).
Klages, K. et al., Selective depletion of Foxp3+ regulatory T cells improves effective therapeutic vaccination against established melanoma, Cancer Res., 70(20):7788-99 (2010).
Ko, K. et al., Treatment of advanced tumors with agonistic anti-GITR mAb and its effects on tumor-infiltrating Foxp3+CD25+CD4+ regulatory T cells, J. Exp. Med., 202(7):885-91 (2005).
Koch, M.A. et al., The transcription factor T-bet controls regulatory T cell homeostasis and function during type 1 inflammation, Nat. Immunol., 10(6):595-602 (2009).
Komatsu, N. and Hori, S., Full restoration of peripheral Foxp3+ regulatory T cell pool by radioresistant host cells in scurfy bone marrow chimeras, Proc. Natl. Acad. Sci. U S A, 104(21):8959-64 (2007).
Lal, G. et al., Epigenetic regulation of Foxp3 expression in regulatory T cells by DNA methylation, J. Immunol., 182(1):259-73 (2009).
Lehtimäki, S. and Lahesmaa, R., Regulatory T Cells Control Immune Responses through Their Non-Redundant Tissue Specific Features, Front. Immunol., 4:294 (2013).
Li, Y. and Xie, X., A mixture model for expression deconvolution from RNA-seq in heterogeneous tissues, BMC Bioinformatics, 14 Suppl 5:S11, 11 pages (2013).
Littman, D.R. and Rudensky, A.Y., Th17 and regulatory T cells in mediating and restraining inflammation, Cell, 140(6):845-58 (2010).
Loi, S. et al., Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98, J. Clin. Oncol., 31(7):860-7 (2013).
Michaud, M. et al., Autophagy-dependent anticancer immune responses induced by chemotherapeutic agents in mice, Science, 334(6062):1573-7 (2011).
Mizukami, Y. et al., Localisation pattern of Foxp3+ regulatory T cells is associated with clinical behaviour in gastric cancer, Br. J. Cancer., 98(1):148-53 (2008).

(56) References Cited

OTHER PUBLICATIONS

Mulligan, A.M. et al., Tumoral lymphocytic infiltration and expression of the chemokine CXCL10 in breast cancers from the Ontario Familial Breast Cancer Registry, Clin. Cancer Res., 19(2):336-46 (2013).
Ott, P.A. et al., CTLA-4 and PD-1/PD-L1 blockade: new immunotherapeutic modalities with durable clinical benefit in melanoma patients, Clin. Cancer Res., 19(19):5300-9 (2013).
Pagès, F. et al., Immune infiltration in human tumors: a prognostic factor that should not be ignored, Oncogene, 29(8):1093-102 (2010).
Pardoll, D.M., The blockade of immune checkpoints in cancer immunotherapy, Nat. Rev. Cancer., 12(4):252-64 (2012).
Peggs, K.S. et al., Blockade of CTLA-4 on both effector and regulatory T cell compartments contributes to the antitumor activity of anti-CTLA-4 antibodies, J. Exp. Med., 206(8):1717-25 (2009).
Peng, G. et al., Toll-like receptor 8-mediated reversal of CD4+ regulatory T cell function, Science, 309(5739):1380-4 (2005).
Pere, H. et al., Comprehensive analysis of current approaches to inhibit regulatory T cells in cancer, Oncoimmunology, 1(3):326-333 (2012).
Perou, C.M., Molecular stratification of triple-negative breast cancers, Oncologist, 16 Suppl 1:61-70 (2011).
Petersen, R.P. et al., Tumor infiltrating Foxp3+ regulatory T-cells are associated with recurrence in pathologic stage I NSCLC patients, Cancer, 107(12):2866-72 (2006).
Piconese, S. et al., OX40 triggering blocks suppression by regulatory T cells and facilitates tumor rejection, J. Exp. Med., 205(4):825-39 (2008).
Prall, F. et al., Prognostic role of CD8+ tumor-infiltrating lymphocytes in stage III colorectal cancer with and without microsatellite instability, Hum. Pathol., 35(7):808-16 (2004).
Robert, C. et al., Ipilimumab plus dacarbazine for previously untreated metastatic melanoma, N. Engl. J. Med., 364(26):2517-26 (2011).
Rubtsov, Y.P. et al., Regulatory T cell-derived interleukin-10 limits inflammation at environmental interfaces, Immunity, 28(4):546-58 (2008).
Samstein, R.M. et al., Extrathymic generation of regulatory T cells in placental mammals mitigates maternal-fetal conflict, Cell, 150(1):29-38 (2012).
Sato, E. et al., Intraepithelial CD8+ tumor-infiltrating lymphocytes and a high CD8+/regulatory T cell ratio are associated with favorable prognosis in ovarian cancer, Proc. Natl. Acad. Sci. U S A, 102(51):18538-43 (2005).
Savage, P.A. et al., Basic principles of tumor-associated regulatory T cell biology, Trends Immunol., 34(1):33-40 (2013).
Scott, A.M. et al., Antibody therapy of cancer, Nat. Rev. Cancer, 12(4):278-87 (2012).
Shalem, O. et al., Genome-scale CRISPR-Cas9 knockout screening in human cells, Science, 343(6166):84-7 (2014).
Sharma, P. et al., Novel cancer immunotherapy agents with survival benefit: recent successes and next steps, Nat. Rev. Cancer, 11(11):805-12 (2011).
Shi, L. et al., Efficacy of adjuvant immunotherapy with cytokine-induced killer cells in patients with locally advanced gastric cancer, Cancer Immunol. Immunother., 61(12):2251-9 (2012).
Shimizu, K. et al., Tumor-infiltrating Foxp3+ regulatory T cells are correlated with cyclooxygenase-2 expression and are associated with recurrence in resected non-small cell lung cancer, J. Thorac. Oncol., 5(5):585-90 (2010).
Simpson, T.R. et al., Fc-dependent depletion of tumor-infiltrating regulatory T cells co-defines the efficacy of anti-CTLA-4 therapy against melanoma, J. Exp. Med., 210(9):1695-710 (2013).
Stephens, G.L. et al., Engagement of glucocorticoid-induced TNFR family-related receptor on effector T cells by its ligand mediates resistance to suppression by CD4+CD25+ T cells, J. Immunol., 173(8):5008-20 (2004).
Suzuki, K. et al., Clinical impact of immune microenvironment in stage I lung adenocarcinoma: tumor interleukin-12 receptor ?2 (IL-12R?2), IL-7R, and stromal FoxP3/CD3 ratio are independent predictors of recurrence, J. Clin. Oncol., 31(4):490-8 (2013).
Takahashi, R. et al., Defective regulatory T cells in patients with severe drug eruptions: timing of the dysfunction is associated with the pathological phenotype and outcome, J. Immunol., 182(12):8071-9 (2009).
Tan, M.G. et al., Disruption of CCR5-dependent homing of regulatory T cells inhibits tumor growth in a murine model of pancreatic cancer, J. Immunol., 182(3):1746-55 (2009).
Teng, M.W. et al., Conditional regulatory T-cell depletion releases adaptive immunity preventing carcinogenesis and suppressing established tumor growth, Cancer Res., 70(20):7800-9 (2010).
Topalian, S. L. et al., Safety, Activity, and Immune Correlates of Anti-PD-1 Antibody in Cancer, The New England Journal of Medicine, 366(26):2443-2454 (2012).
Turk, M.J. et al., Concomitant tumor immunity to a poorly immunogenic melanoma is prevented by regulatory T cells, J. Exp. Med., 200(6):771-82 (2004).
Valzasina, B, et al., Triggering of OX40 (CD134) on CD4(+)CD25+ T cells blocks their inhibitory activity: a novel regulatory role for OX40 and its comparison with GITR, Blood, 105(7):2845-51 (2005).
Verbsky, J.W. and Chatila, T.A., Immune dysregulation, polyendocrinopathy, enteropathy, X-linked (IPEX) and IPEX-related disorders: an evolving web of heritable autoimmune diseases, Curr. Opin. Pediatr., 25(6):708-14 (2013).
Viguier, M. et al., Foxp3 expressing CD4+CD25(high) regulatory T cells are overrepresented in human metastatic melanoma lymph nodes and inhibit the function of infiltrating T cells, J. Immunol., 173(2):1444-53 (2004).
Wang, L. et al., Foxp3+ T-regulatory cells require DNA methyltransferase 1 expression to prevent development of lethal autoimmunity, Blood, 121(18):3631-9 (2013).
Wolf, D. et al., The expression of the regulatory T cell-specific forkhead box transcription factor FoxP3 is associated with poor prognosis in ovarian cancer, Clin. Cancer Res., 11(23):8326-31 (2005).
Yagi, H. et al., Crucial role of FOXP3 in the development and function of human CD25+CD4+ regulatory T cells, Int. Immunol., 16(11):1643-56 (2004).
Yan, M. et al., Recruitment of regulatory T cells is correlated with hypoxia-induced CXCR4 expression, and is associated with poor prognosis in basal-like breast cancers, Breast Cancer Res., 13(2):R47 (2011).
Yang, H. et al., One-step generation of mice carrying reporter and conditional alleles by CRISPR/Cas-mediated genome engineering, Cell, 154(6):1370-9 (2013).
Zheng, Y. et al., Regulatory T-cell suppressor program co-opts transcription factor IRF4 to control T(H)2 responses, Nature, 458(7236):351-6 (2009).
Zhou, S. et al., CCR7 expression and intratumoral FOXP3+ regulatory T cells are correlated with overall survival and lymph node metastasis in gastric cancer, PLoS One, 8(9):e74430 (2013).
Author Not Known, MJ [G11] (ATCC® CRL8294™), Product Sheet, American Type Culture Collection, 3 pages (2013).
Gao, J. et al., Integrative Analysis of Complex Cancer Genomics and Clinical Profiles Using the cBioPottal, Sci Signal., 6(269):pl1, 34 pages (2014).

\* cited by examiner

PANELS A-C

PANELS A-B

PANELS, A-C

PANELS A-B

PANELS A-B

DEPLETING TUMOR-SPECIFIC TREGS

BACKGROUND

Significant effort has been invested in the identification and/or development for promoting ability of the immune system to target and destroy tumors. Unfortunately, so far, success has proven elusive. Indeed, although therapeutic modulation of the immune system in cancer patients through, for example, antibody blockage of inhibitory molecules, adoptive T cell transfer, vaccination and other methods has shown some clinical benefit, patient responses have been variable at best.

SUMMARY

The present invention provides technologies for treating cancer by depleting Treg cells. In particular, the present invention demonstrates that targeting CCR8 can achieve specific depletion of Treg cells as compared with other immune cells including specifically CD4 and/or CD8 cells.

Prior to the present disclosure, techniques were not available for targeting Treg cells without also potentially targeting other immune cells. Given that inadvertent targeting of other immune cells might inhibit, rather than propose, an anti-tumor immune response, prior to the present disclosure those skilled in the art might reasonably be discouraged or dissuaded from attempting therapeutic strategies directed at Treg depletion. The present invention, however, provides mechanisms for specifically targeting Treg cells, as compared with other immune cells, for depletion. In particular, the present disclosure demonstrates the feasibility and effectiveness of targeting CCR8 to achieve specific depletion of Treg cells as compared with CD4 and CD8 cells.

In some embodiments, the present invention provides technologies for the diagnosis and/or treatment of cancer by targeting CCR8, for example through administration of compositions comprising CCR8-targeting agents.

In some embodiments, the present invention provides technologies for the identification and/or characterization of agents useful in the diagnosis and/or treatment of cancer through detection and/or analysis of agents that specifically target CCR8. In some embodiments, the present invention provides technologies for the identification and/or characterization of agents useful in the diagnosis and/or treatment of cancer through detection and/or analysis of binding to CCR8. In some embodiments, the present invention provides technologies for the identification and/or characterization of agents useful in the diagnosis and/or treatment of cancer through detection and/or analysis of depletion of tumor-infiltrating Treg cells.

In some embodiments, the present invention provides methods of treating cancer by targeting CCR8 in a subject having a tumor, so that tumor-infiltrating Treg cells are depleted in the subject. In some such embodiments, the targeting CCR8 comprises administering to the subject a composition comprising a CCR8-targeting agent that depletes tumor-infiltrating Treg cells. In some embodiments the CCR8-targeting agent binds specifically to CCR8 in or on tumor-infiltrating Treg cells. In some particular embodiments, the CCR8-targeting agent is or comprises an antibody agent. In some embodiments, the CCR8-targeting agent comprises a payload moiety so that, when the CCR8-targeting agent is delivered to tumor-infiltrating Treg cells, such cells are depleted from the tumor.

Alternatively or additionally, in some embodiments, CCR8-targeting methods of the present invention further comprise administering one or more immunomodulatory therapeutic modalities to the subject.

In some embodiments, the present invention provides methods of detecting and/or characterizing a tumor, and/or Tregs infiltrating it, by administering to a subject having the tumor a composition comprising a CCR8-targeting agent in association with a detectable moiety, so that tumor-infiltrating Treg cells are detected. In some embodiments, such methods further comprise, prior to and/or after the detecting and/or characterizing, treating the subject in which tumor-infiltrating Treg cells are detected by targeting CCR8. In some embodiments, provided methods include selecting subjects and/or tumors for treatment for CCR8-targeted therapy and/or for anti-tumor immunomodulatory therapy. Alternatively or additionally, in some embodiments, provided methods include monitoring progress of cancer and/or of therapy.

Alternatively or additionally, in some embodiments, CCR8-targeting methods of the present invention further comprise targeting CCR4. In some such embodiments, targeting CCR4 comprises administering to the subject a composition comprising a CCR4-targeting agent. In some particular embodiments, the CCR4-targeting agent is or comprises a bifunctional agent that targets both CCR8 and CCR4.

In some embodiments, the present invention provides methods of identifying and/or characterizing one or more CCR8-targeting agents by contacting the one or more agents with CCR8 and determining their ability to bind specifically to CCR8. In some such embodiments, the step of contacting comprises contacting with isolated CCR8, for example by contacting with cells expressing CCR8, and/or with tissue is which CCR8 is expressed. In some embodiments, the step of contacting comprises administering to an organism comprising tissue or cells in which CCR8 is expressed.

In some embodiments, of provided methods of identifying and/or characterizing one or more CCR8-targeting agents by contacting the one or more agents with CCR8 and determining their ability to bind specifically to CCR8, the step of determining comprises detecting specific binding of the one or more agents (e.g., one or more antibody agents) to tumor-infiltrating Treg cells in the organism.

In some embodiments, the present invention provides methods of identifying and/or characterizing one or more CCR8-targeting agents by contacting the one or more agents with a tumor comprising tumor-infiltrating Treg cells and determining their ability to deplete the tumor-infiltrating Treg cells from the tumor. In some such embodiments, the step of contacting comprises administering to an organism having the tumor.

Definitions

In order for the present invention to be more readily understood, certain terms are first defined below. Additional definitions for the following terms and other terms are set forth throughout the specification.

Activates: As used herein, the term "activates" refers to increasing the level and/or activity of a target.

Activating agent: As used herein, the term "activating agent" refers to an agent whose presence or level correlates with elevated level and/or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control). In some embodiments, an activating agent i) stimulates, promotes, or increases level and/or activity of another entity and/or ii) stimulates, promotes, accelerates (e.g., timing and/or frequency of) or increases one or more effects of such other entity; and/or ii) inhibits, decreases, reduces, or delays one or more biological events.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance Animal: As used herein, the term "animal" refers to any member of the animal kingdom. In some embodiments, "animal" refers to a human, at an appropriate stage of development (including any stage). In some embodiments, "animal" refers to a non-human animals, at an appropriate stage of development (including any stage). In certain embodiments, a non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal is a vertebrate. In some embodiments, an animal may be a transgenic animal, genetically-engineered animal, and/or a clone.

Antagonist: As used herein, the term "antagonist" refers to an agent whose presence or level correlates with reduced level or activity of a target, as compared with that observed absent the agent (or with the agent at a different level). In some embodiments, an antagonist is an agent whose presence or level correlates with a target level or activity that is comparable to or less than a particular reference level or activity (e.g., that observed under appropriate reference conditions, such as presence of a known antagonist (e.g., a positive control). In some embodiments, the term "antagonist" refers to an agent that i) inhibits, decreases or reduces level and/or activity of another entity and/or ii) inhibits, decreases, delays or reduces one or more effects of such other entity; and/or ii) inhibits, decreases, reduces, or delays one or more biological events. Antagonists may be or include agents of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, for example so that level or activity of the target is altered). In some embodiments, action of an antagonist may be reversible; in some embodiments it may be irreversible. In some embodiments, an antagonist may form a covalent bond with its target; in many such embodiments, the antagonist acts as an irreversible inhibitor of that target. In some embodiments, an antagonist interacts with an active site on its target (e.g., a site of interaction with a partner entity or substrate). In some embodiments, an antagonist competes with another entity (e.g., a partner binding agent or a substrate) for interaction with a target.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Antigen: As used herein, the term "antigen" refers to a molecule or entity to which an immunoglobulin specifically binds. In some embodiments, an antigen is or comprises a polypeptide or portion thereof. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: As used herein, the term "binding" refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g., phosphate-buffered saline), sterile saline solution, Ringer's solution or dextrose solution.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance; epitope-binding specificity is one example. In some embodiments, a characteristic portion may be biologically active.

Combination therapy: As used herein, the term "combination therapy" refers to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially such that the agents have simultaneous biologically activity with in a subject.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Dendritic cell: As used herein, the term "dendritic cell" refers to particular immune cells that process antigen material and present it on the surface to other cells of the immune system. Dendritic cells act as messengers between the innate and adaptive immunity and are communicating with other cells through direct contact or at a distance using cytokines. Reacting to the presence of foreign antigens, dendritic cells produce cytokines which in turn induce other immune cells, T cells for example, to aid in the immune response.

Diagnostic information: As used herein, the term "diagnostic information" or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, the term "gene" has its meaning as understood in the art. In some embodiments, the term "gene" may include gene regulatory sequences (e.g., promoters, enhancers, etc.) and/or intron sequences. In some embodiments, the term refers to nucleic acids that do not encode proteins but rather encode functional RNA molecules such as tRNAs, RNAi-inducing agents, etc. Alternatively or additionally, in many embodiments, the term "gene", as used in the present application, refers to a portion of a nucleic acid that encodes a protein. Whether the term encompasses other sequences (e.g., non-coding sequences, regulatory sequences, etc) will be clear from context to those of ordinary skill in the art.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Improve, increase, or reduce: As used herein, the terms "improve," "increase" or "reduce," or grammatical equivalents, indicate values that are relative to an appropriate baseline or reference level or amount. Those of ordinary skill in the art will be aware of appropriate reference levels or amount for particular values of interest in accordance with the present invention. To give but a few examples, in some embodiments, a reference level or amount is that determined under otherwise comparable conditions (e.g., in the same system or individual) absent administration of a particular agent. In some embodiments a reference level or amount is that determined in an appropriate comparator system, individual, or population (e.g., in a system, individual or population not afflicted with or representative of a particular disease, disorder or condition).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell that is not presently part of a multi-cellular organism.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes inflammation.

Pharmaceutically acceptable: As used herein, the term "pharmaceutically acceptable", refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Prevent: As used herein, the term "prevent" or "prevention", when used in connection with the occurrence of a disease, disorder, and/or condition, refers to reducing the risk of developing the disease, disorder and/or condition and/or to delaying the onset of one or more symptoms or characteristics of the disease, disorder, or condition. See the definition of "risk."

Prognostic and predictive information: As used herein, the terms "prognostic and predictive information" are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest Response: As used herein, a "response" to treatment may refer to any alteration in a subject's condition that occurs as a result of or correlates with treatment. Such alteration may include a beneficial alteration, such as stabilization of the condition (e.g., prevention of deterioration that would have taken place in the absence of the treatment), amelioration of symptoms of the condition, and/or improvement in the prospects for cure of the condition, etc. It may refer to a subject's response. Subject response may be measured according to a wide variety of criteria, including clinical criteria and objective criteria. In some embodiments, a response may include an alteration that is not beneficial (e.g., a side effect).

Risk: As will be understood from context, a "risk" of a disease, disorder, and/or condition comprises a likelihood that a particular individual will develop a disease, disorder, and/or condition (e.g., cancer). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., cancer). In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, a sample obtained from a subject may include, but is not limited to, one or more of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. Specificity may be evaluated in the context of additional factors such as the affinity of the binding molecule for the target molecule versus the affinity of the binding molecule for other targets (e.g., competitors). If a binding molecule exhibits a high affinity for a target molecule that it is desired to detect and low affinity for non-target molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

T cell: As used herein, the term "T cell" refers to a lymphocyte (e.g., white blood cell) that functions in cell-mediated immunity. In some embodiments, the presence of a T cell receptor (TCR) on the cell surface distinguishes T cells from other lymphocytes. As is known in the art, T cells typically do not present antigens, and rely on other lymphocytes (e.g., natural killer cells and B cells) to aid in antigen presentation. Types of T cells include: T helper cells (TH cells), Memory T cells (Tcm, Tem, or Temra), Regulatory T cells (Treg), Cytotoxic T cells (CTLs), Natural killer T cells (NK cells), gamma delta T cells, and Mucosal associated invariant T cells (MAIT).

Therapeutic agent: As used herein, the phrase "therapeutic agent" refers to any agent that has a therapeutic effect and/or elicits a desired biological and/or pharmacological effect, when administered to a subject.

Therapeutically effective amount: As used herein, the term "therapeutically effective amount" refers to an amount of a therapeutic agent (e.g., bacterial metabolites, short chain fatty acids, HDAC inhibitors) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Treg cells: As used herein, the term Treg cell refers to Regulatory T cells (Treg), also sometimes referred to as Suppressor T cells. Treg cells maintain immunological tolerance. During an immune response, Tregs stop T cell-mediated immunity and suppress auto-reactive T cells that have escaped negative selection within the thymus. Treg cells have also been described as able to suppress other types of immune cells such as NK cells and B cells. Adaptive Treg cells (called Th3 or Tr1 cells) are thought to be generated during an immune response. Naturally occurring Treg cells (CD4+CD25+FoxP3+ Treg cells) are generated in the thymus and have been linked to interactions between developing T cells with both myeloid (CD11c+) and plasmacytoid (CD123+) dendritic cells that have been activated with the cytokine thymic stromal lymphopoietin (TSLP). The presence of FoxP3 in naturally occurring Treg cells distinguishes them from other T cells. Mutations of the FOXP3 gene can prevent regulatory T cell development, causing the fatal autoimmune disease IPEX. In some embodiments, Treg cells and/or populations thereof are defined by presence of particular surface markers. In some embodiments, human Treg cells and/or populations thereof, are defined by CD3+ CD4+CD45RA-CD45RO+CD25+ (>95% Foxp3+, FIG. 4).

BRIEF DESCRIPTION OF THE DRAWING

FIG. 1, comprised of Panels A-C, illustrates how Ablation of Treg cells affects the growth of fully established primary and lung metastatic tumors. (A) Flow cytometric quantification of intratumoral $CD4^+$ $Foxp3^+$ T cells (left panel) and IFN-γ production in T cells (right panels). Top: control, Bottom: DT-treated. (B) Growth kinetics of orthotopic tumors in mice treated with 50 μg/kg DT when tumors reached approximately 250 $mm^3$. Representative of two independent experiments; n=5 mice per group; p<0.0001**** (C) Fraction and representative image of mice with detectable lung metastasis upon bioluminescence imaging of the dissected lungs from the group depicted in (B).

FIG. 1, comprised of Panels A-B, depicts levels of Treg cells present in various human cancers (specifically, breast carcinoma, melanoma, and colon carcinoma), and of CD4+ tumor infiltrating lymphocytes in human breast carcinoma. (A) Gates indicate $CD4^+Foxp3^+$ Treg. Ratio of CD8 to CD4 T cell yields. (B) Thirty-five human breast tumor samples were processed and CD4 and CD8 T cell subsets isolated by fluorescence activated cell sorting. Graph indicates the ratio of CD8 to CD4 T cell yields.

FIG. 3, comprised of Panels A-C, depicts selective infiltration of breast cancers by Treg cells. $CD3^+$ T cells from normal breast parenchyma and tumor infiltrating lymphocytes from human breast carcinoma (A). Gates indicate % of $CD4^+Foxp3^+$ Treg. Lymphocytes isolated from normal breast parenchyma and breast cancer from the same patient were stimulated in vitro with PMA/Ionomycin and analyzed for intracellular cytokine production of IFNγ (B) and TNFα (C). Gates indicate % of cytokine producing CD3+ T cells.

FIG. 4 shows fluorescence activated cell sorting strategy for isolation of Treg from human breast tumors. Treg (defined as $CD3^+CD4^+CD45RA^-$ $CD45RO^+CD25^+$) are 95% $Foxp3^+$ following intracellular staining and flow cytometry analysis with a Foxp3-specific antibody. Foxp3 is a Treg specific transcription factor.

FIG. 5 depicts levels of CCR8 mRNA transcripts in FACS-isolated tumor-infiltrating CD8 T cells (tCD8), CD4 T cells (tCD4), Treg cells (tTreg), as well as in normal blood CD4 T cells (bCD4), and Treg cells (bTreg).

FIG. 6 shows CCR8 protein expression by flow cytometric analysis of human T cells from an invasive breast ductal carcinoma, normal glandular breast tissue, and an adenocarcinoma of the colon.

FIG. 7 shows CCR8 and CCR4 protein expression by flow cytometric analysis of human T cells infiltrating an invasive breast ductal carcinoma.

FIG. 8 shows a schematic of a mixed bone marrow chimera experiment. This experimental strategy takes advantage of the fact that T cell deficient mice reconstituted with bone marrow from FOXP3$^{-/-}$ mice do not have any Treg cells as FOXP3 is the master transcriptional regulator of Treg cell development and function. Tcr beta delta deficient ($\beta\delta-/-$) mice were sublethaly irradiated and reconstituted with FOXP3-/- bone marrow and an equal amount of either wild type (WT) or CCR8$^{-/-}$ bone marrow. The resulting mice are mixed bone marrow chimeras with Group 1 only having WT Treg cells and Group 2 only having CCR8$^{-/-}$ Treg cells. The remaining immune cells are a mixture of the donor bone marrows.

FIG. 9 shows CCR8 expressing Treg cells promote primary and metastatic mammary tumor progression. A mammary carcinoma cell line generated from C57BL/6 mice expressing a transgene encoding the PyMT oncogene under control of the MMTV promoter experimental groups were implanted in the mammary fat pads of mice from the experimental groups outlined in FIG. 1. Primary tumor growth was assessed by serial volume measurements and metastatic lung burden was assessed by counting lung tumors from sacrificed animals under a dissecting microscope. A. Mice lacking CCR8 expressing Treg cells exhibit delayed primary tumor growth as compared to the control group. B. The lack of CCR8 expression on Treg cells also leads to a significant reduction in metastatic lung burden.

FIG. 10 shows CCR8 expression on human tumor infiltrating Treg cells correlates with Treg cell proliferation and higher tumor grade. Tumor infiltrating Treg cell proliferative status (Ki67 expression) and CCR8 expression was determined by flow cytometry of tumor infiltrating lymphocytes from fresh primary human breast carcinomas. A. Treg cell Ki67 expression positively correlates with Treg cell CCR8 expression. Ki67 expression is indicated as the % of Treg cells expressing the proliferation marker Ki67. CCR8 expression of Treg cells is indicated as a ratio of the mean fluorescence intensity (MFI) of CCR8 staining divided by that of effector CD4 T cells. B. CCR8 expression on tumor infiltrating Treg cells is associated with higher tumor grade.

DETAILED DESCRIPTION OF CERTAIN EMBODIMENTS

Figure 1:
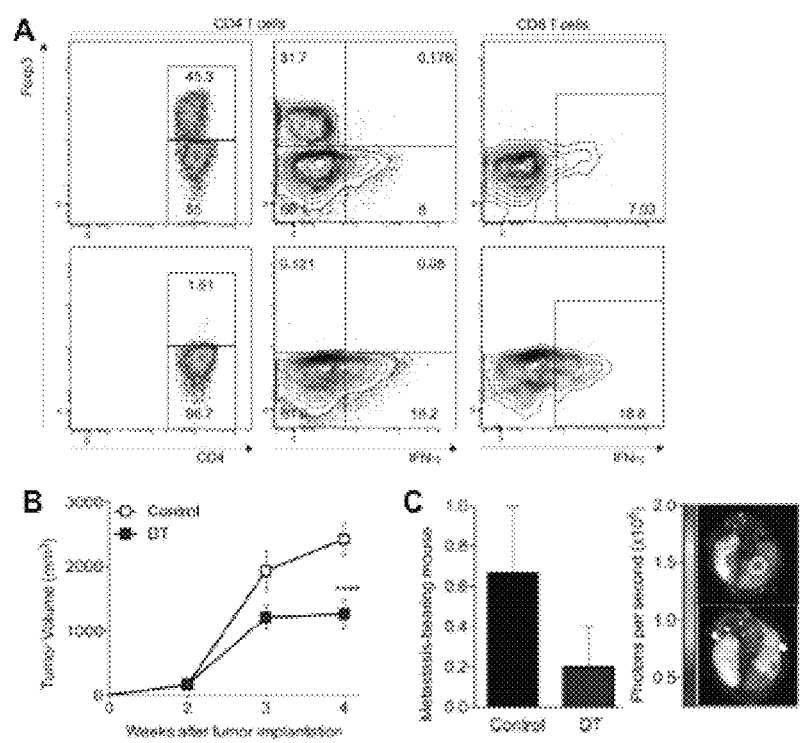
FIG. 1, Panels A-C.
Figure 2:
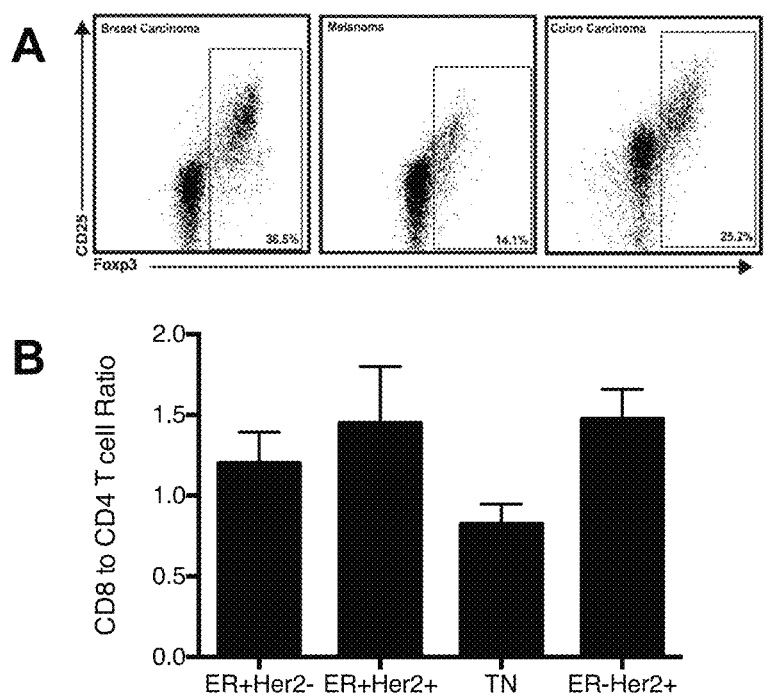
FIG. 2, Panels A-B.
Figure 3:
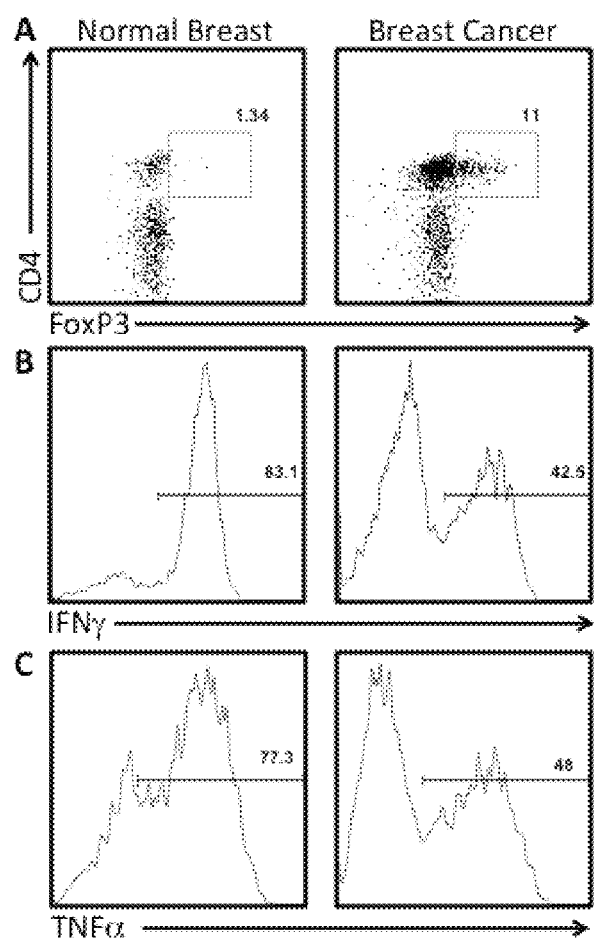
FIG. 3, Panels A-C.

The present invention demonstrates, among other things, that CCR8 is highly and specifically expressed by tumor-infiltrating Treg cells (as compared, for example, to tumor-infiltrating effector T cells), and furthermore demonstrates the generality of this phenomenon across a variety of tumor types. The present invention provides methods and compositions for the treatment of cancer by targeting CCR8, and/or for identifying and/or characterizing useful cancer therapeutic and/or diagnostic agents that target CCR8.

Trees and Immune Evasion

The solid tumor microenvironment contains a variety of immune cells. Extensive human and mouse experimental studies suggest that the types and properties of the immune cells residing within a tumor influence clinical response (Refs: 11 and 12, and 22-30). In particular, regulatory T (Treg) cell presence is associated with poor clinical outcome in melanoma (Ref: 22), breast (Refs: 23-24) gastric (Ref: 25), ovarian (Ref: 26), pancreatic (Ref: 27) and other cancer types, while a high CD8+ tumor infiltrating lymphocyte (TIL) density correlates with improved survival in several cancer types (Refs: 12, and 28-30). In large cohorts of human colorectal tumors, immunological parameters (type, density, location of immune cells within a tumor) were a better predictor of survival than the current histopathological methods used for staging (Ref: 11).

Regulatory T cells (Treg) are a subset of CD4 T cells that are required for control of autoimmunity, dampening excessive inflammation caused by the immune response to pathogens, and maintaining maternal-fetal tolerance (Refs 6-8). Regulatory T cells (Treg) are important in maintaining homeostasis, controlling the magnitude and duration of the inflammatory response, and in preventing autoimmune and allergic responses. There are two major classifications of Treg: natural Treg and peripheral Treg. Natural Treg, (nTreg) are a class of thymically generated T-cells while peripheral Treg (pTreg) develop in the periphery from naïve T cells in response to signals such as low doses of antigen, presence of certain microbes, lymphopenia or, in some cases, through activation by immature dendritic cells. In some cases, pTreg are thought to be generated in response to inflammatory conditions, particularly those which may be due at least in part to the absence of nTreg cells.

The Forkhead box P3 transcription factor (Foxp3) has been shown to be a key regulator in the differentiation and activity of Treg. In fact, loss-of-function mutations in the Foxp3 gene have been shown to lead to the lethal IPEX syndrome (immune dysregulation, polyendocrinopathy, enteropathy, X-linked). Patients with IPEX suffer from severe autoimmune responses, persistent eczema, and colitis.

In general Tregs are thought to be mainly involved in suppressing immune responses, functioning in part as a "self-check" for the immune system to prevent excessive reactions. In particular, Tregs are involved in maintaining tolerance to self-antigens, harmless agents such as pollen or food, and abrogating autoimmune disease.

Tregs are found throughout the body including, without limitation, the gut, skin, lung, and liver. Additionally, Treg cells may also be found in certain compartments of the body that are not directly exposed to the external environment such as the spleen, lymph nodes, and even adipose tissue. Each of these Treg cell populations is known or suspected to have one or more unique features and additional information may be found in Lehtimaki and Lahesmaa (Regulatory T cells control immune responses through their non-redundant tissue specific features, FRONTIERS IN IMMUNOL., 4(294): 1-10, 2013), the disclosure of which is hereby incorporated in its entirety.

Typically, regulatory T cells are known to require TGF-$\beta$ and IL-2 for proper activation and development. Blockade of TGF-$\beta$ signaling has been shown to result in systemic inflammatory disease as a result of a deficiency of Treg and IL-2 knockout mice have been shown to fail to develop Treg. TGF-$\beta$ may be particularly important, as it is known to stimulate Foxp3, the transcription factor that drives differentiation of T cells toward the Treg lineage.

Tregs are known to produce both IL-10 and TGF-β, both potent immune suppressive cytokines. Additionally, Tregs are known to inhibit the ability of antigen presenting cells (APCs) to stimulate T cells. One proposed mechanism for APC inhibition is via CTLA-4, which is expressed by Foxp3$^+$ Treg. It is thought that CTLA-4 may bind to B7 molecules on APCs and either block these molecules or remove them by causing internalization resulting in reduced availability of B7 and an inability to provide adequate co-stimulation for immune responses. Additional discussion regarding the origin, differentiation and function of Treg may be found in Dhamne et al., Peripheral and thymic Foxp3+ regulatory T cells in search of origin, distinction, and function, 2013, Frontiers in Immunol., 4 (253): 1-11, the disclosure of which is hereby incorporated in its entirety.

While Tregs are critical for maintaining peripheral tolerance, their potent immunoregulatory properties can promote the development of numerous types of malignancies (Refs 9, 10) by inhibiting effector responses. For many cancers, the presence of large numbers of Treg cells correlates with poor outcome (Ref 10 and 98). Furthermore, clinical evaluation of human breast cancers reveals that the prevalence of Treg among tumor infiltrating lymphocytes increases with disease stage. A decrease in the number of breast tumor infiltrating Tregs is positively associated with a pathological response to neoadjuvant chemotherapy. (Refs 59 and 60). Preliminary data reveal that the specific ablation of Treg in advanced murine breast tumors leads to a significant delay in tumor growth and a dramatic reduction in metastatic burden. (Ref 9)

The present invention encompasses the recognition that Tregs integrate external local cues to modulate specific segments of their transcriptomic program, and they do so by a set of common regulators they share with the ongoing immune response. Without wishing to be bound by any particular theory, the present invention proposes that the tumor microenvironment also induces a Treg-specific transcriptional program. The present invention further proposes that effective strategies for targeting tumor-infiltrating Tregs can be developed through an understanding of this transcriptional program.

Prior to the present disclosure, data regarding the consequences of the tumor microenvironment on human Treg populations was limited. As described herein, the present inventors isolated Treg cells, effector CD4 T cells and CD8 T cells from breast infiltrating duct carcinomas as well as from normal breast parenchyma and peripheral blood for in depth transcriptome analysis by RNAseq. Among other things, this work revealed targets for therapeutic depletion of Treg from the tumor microenvironment. Specifically, work described herein revealed that CCR8 is a useful target specific to tumor-infiltrating Treg cells.

CCR8

CCR8 is a member of the β-chemokine receptor family, which is predicted to be a seven transmembrane protein similar to G protein-coupled receptors. Chemokines and their receptors are known to be important for the migration of various cell types into the inflammatory sites.

CCR8 has been reported to play a role in regulation of monocyte chemotaxis and thymic cell apoptosis. More specifically, it has been suggested that CCR8 may contribute to proper positioning of activated T cells within antigenic challenge sites and specialized areas of lymphoid tissues.

In humans, the gene encoding CCR8 is located in the chemokine receptor gene cluster region 3p22.

Identified ligands of CCR8 include its natural cognate ligand, CCL1 (aka 1-309), thymus activation-regulated cytokine (TARC) and macrophage inflammatory protein-1 beta (MIP-1 beta).

CCR8 is preferentially expressed in the thymus, and recent reports have indicated that its expression is elevated in human cancer tissues, primarily limited to tumor-associated macrophages (see Eruslanov et al, Clin Cancer Res. 19:1670, Epub 2013 Jan. 30). The present disclosure provides the surprising demonstration that, in fact, CCR8 is specifically expressed in Treg cells, and more particularly in tumor-infiltrating Tregs. The present disclosure specifically teaches that CCR8 is specifically expressed in tumor-infiltrating Tregs as compared with other tumor-infiltrating T cell subsets (i.e., tumor infiltrating CD4 and CD8 T cells), and demonstrates that CCR8 can serve as an effective target to mediate depletion of such tumor-infiltrating Treg cells.

CCR8-Targeting Agents

In light of the provided teaching that CCR8 can effectively be targeted to achieve specific depletion of Treg cells, and particularly of tumor-infiltrating Treg cells, those skilled in the art will appreciate that any of a variety of appropriate agents may be used to target CCR8 and achieve such depletion.

agents that bind specifically to CCR8, or to nucleic acids encoding it. In some embodiments, the present invention provides systems for identifying and/or characterizing agents that target CCR8 on the surface of Treg cells, and most particularly on the surface of tumor-infiltrating Treg cells. In some embodiments, the present invention provides systems for identifying and/or characterizing agents (e.g., siRNAs, antisense nucleic acids, CRISPR™ agents, or other nucleic acid binding and/or modifying agents) that bind specifically to CCR8-encoding nucleic acids (e.g., DNA or RNA such as genomic DNA or any transcript thereof), and block or inhibit its expression (e.g., by blocking or inhibiting transcription, transport, splicing, and/or translation of the relevant nucleic acid(s)).

In some embodiments, a CCR8-targeting agent for use in accordance with the present invention is or comprises a CCR8-specific antibody or antigen-binding fragment thereof. In some embodiments, an CCR8-targeting agent is or comprises an antibody or antigen-binding fragment thereof that binds to a CCR8 polypeptide found on surfaces of Treg cells, and particularly on surfaces of Treg cells that have infiltrated a tumor.

In some embodiments, a CCR8-targeting agent that is or comprises an antibody may be or comprise an antibody, or fragment thereof, of any appropriate isotype, including, for example: IgG (e.g., IgG1, IgG2, IgG3, IgG4), IgM, IgA1, IgA2, IgD, or IgE. In some embodiments, an antibody, or fragment thereof, is an IgG isotype, e.g., IgG1 or IgG4.

In some embodiments, a CCR8-targeting agent may be or comprise a full-length antibody. In some embodiments, a CCR8-targeting agent may be or comprise only an antigen-binding fragment (e.g., a Fab, F(ab)2, Fv or single chain Fv fragment) of an antibody (e.g., an may lack or be substantially free of other antibody components). In some embodiments, an a CCR8-targeting agent may be or comprise multiple antigen-binding components of an antibody (e.g., as in a diabody or zybody). In some embodiments, a CCR8-targeting agent may include one or more CDRs found in a full-length antibody raised in an organism against the relevant antigen (i.e., against CCR8). In some embodiments, a CCR8-targeting agent may include such CDRs in a different polypeptide context than that in which they are found in the organism-raised antibody.

In some embodiments, a CCR8-targeting agent may be or comprise an antibody, or fragment thereof, that is monoclonal, recombinant, chimeric, deimmunized, human, humanized, etc as these terms are understood in the art.

In some embodiments, a CCR8-targeting agent may be or comprise an antibody Fc region; in some such embodiments, the Fc region may be glycosylated. In some embodiments, such an Fc region may be engineered so that it is glycosylated and/or otherwise modified in a manner that modifies its affinity for, and/or one or more other characteristics of binding with Fc receptors on effector cells relative to that observed with an otherwise comparable or identical Fc region lacking the modification. In some embodiments, a utilized Fc region is engineered to be modified (e.g., glycosylated) so that its affinity for one or more Fc receptors on an effector cell is increased relative to that observed with an otherwise comparable or identical Fc region lacking the modification.

As is known in the art, monoclonal antibodies can be produced by a variety of techniques, including conventional monoclonal antibody methodology, e.g., the standard somatic cell hybridization technique of Kohler and Milstein, Nature 256: 495, 1975. Polyclonal antibodies can be produced by immunization of animal or human subjects. See generally, Harlow, E. and Lane, D. *Antibodies: A Laboratory Manual*, Cold Spring Harbor Laboratory Press, Cold Spring Harbor, N.Y., 1988. Recombinant, chimeric, deimmunized, human, or humanized antibodies can also be produced using standard techniques, as is known in the art. Techniques for engineering and preparing antibodies are described, for example, in U.S. Pat. No. 4,816,567, issued Mar. 28, 1989; U.S. Pat. No. 5,078,998, issued Jan. 7, 1992; U.S. Pat. No. 5,091,513, issued Feb. 25, 1992; U.S. Pat. No. 5,225,539, issued Jul. 6, 1993; U.S. Pat. No. 5,585,089, issued Dec. 17, 1996; U.S. Pat. No. 5,693,761, issued Dec. 2, 1997; U.S. Pat. No. 5,693,762, issued Dec. 2, 1997; U.S. Pat. No. 5,869,619; issued 1991; U.S. Pat. No. 6,180,370, issued Jan. 30, 2001; U.S. Pat. No. 6,548,640, issued Apr. 15, 2003; U.S. Pat. No. 6,881,557, issued Apr. 19, 2005; U.S. Pat. No. 6,982,321, issued Jan. 3, 2006; incorporated herein by reference. Antibodies described herein can be used, e.g., for detection (e.g., diagnostic) assays, and/or for therapeutic applications.

The present disclosure particularly describes use of T-cell depleting agents (e.g., antibody agents) that target CCR8. A variety of CCR8-specific antibodies are known in the art (see, for example, those described in Ref 95). Certain CCR8-antagonists, which in certain embodiments may be useful to deplete Treg cells as described herein, have also been reported (See Ref 96). Those skilled in the art will appreciate that known CCR8 antibodies or antagonists, or fragments thereof, may be utilized in accordance with the present invention. Alternatively or additionally, those skilled in the art will appreciate that new CCR8-specific antibodies may be raised, and screened or selected for cell-depleting activity, in accordance with well-established procedures known in the art (see, for example, Ref 97).

Those skilled in the art will appreciate that useful CCR8-targeting agent for use in accordance with the present invention are not limited to cell-depleting antibody agents, or even to any antibody agents. Other agents that specifically interact with CCR8, and particularly with CCR8 on surfaces of Treg cells, particularly tumor-infiltrating Treg cells, are useful as described herein. In some embodiments, such agents may be or comprise small molecule agents. In some embodiments, such agents may be or comprise peptide agents. In some embodiments, such agents may be or comprise one or more CCR8 ligands, or variants thereof.

In some embodiments of the present invention, a CCR8-targeting agent may be utilized in association with a payload moiety such as a detectable moiety or a therapeutic (e.g., toxic, anti-proliferative, pro-apoptotic, etc) moiety, in order to detect and/or deplete tumor-infiltrating Treg cells as described herein. In some embodiments, association of a CCR8-targeting entity with a payload is covalent.

For example, in some embodiments, a CCR8-targeting agent as described herein is provided and/or utilized in association with a payload that is or comprises a detectable moiety such as a radioactive, fluorescent, chemiluminescent, and/or phosphorescent moiety.

In some embodiments, in some embodiments, a CCR8-targeting agent as described herein is utilized in association with a payload that is or comprises a therapeutic moiety (as is reviewed, for example, with respect to antibody-drug conjugates in Ducry et al Bioconjugate Chem 21:5, 2010; Anderl et ao Methods Mol Biol 1045:51, 2013). To give but a few examples, in some embodiments, a CCR8-targeting agent is provided and/or utilized in association with an anti-proliferative moiety, a pro-apoptotic moiety, or with any other moiety whose specific delivery to tumor-infiltrating Treg cells depletes such cells from the tumor.

In some particular embodiments, a therapeutic moiety may be or comprise a radioactive moiety or another cell-killing moiety (e.g., a chemotherapeutic moiety, a cytotoxic moiety, etc). In some embodiments, a cell-killing moiety can be or comprise a small molecule moiety. In some embodiments, a cell-killing moiety can be or comprise a peptide moiety. In some embodiments, a cell-killing moiety may be or comprise a toxin or toxin-like (see, for example, those provided by Targa Therapeutics, www.targetherapeutics.com/payloads.html) moiety.

Identifying and/or Characterizing CCR8-Targeting Agents

In some embodiments, the present invention provides systems for identifying and/or characterizing agents useful in the diagnosis and/or treatment of cancer, and particularly provides systems for identifying and/or characterizing agents that bind specifically to CCR8, or to nucleic acids encoding it. In some embodiments, the present invention provides systems for identifying and/or characterizing agents that target CCR8 on the surface of Treg cells, and most particularly on the surface of tumor-infiltrating Treg cells. In some embodiments, the present invention provides systems for identifying and/or characterizing agents (e.g., siRNAs, antisense nucleic acids, CRISPR™ agents, or other nucleic acid binding and/or modifying agents) that bind specifically to CCR8-encoding nucleic acids (e.g., DNA or RNA such as genomic DNA or any transcript thereof), and block or inhibit its expression (e.g., by blocking or inhibiting transcription, transport, splicing, and/or translation of the relevant nucleic acid(s)). Those skilled in the art are aware of the multiple available technologies for designing, producing, identifying, and/or characterizing effective such nucleic acid binding agents based on the known sequence of CCR8-encoding nucleic acids.

In light of the disclosure provided herein, that CCR8 is specifically expressed by Treg cells, and particularly by tumor-infiltrating Treg cells, those skilled in the art will appreciate that agents specifically targeting CCR8 are useful in a variety of contexts, including as particularly described herein, and will be aware of a variety of assay formats that can be utilized to identify and/or characterize such agents.

For example, in some embodiments, CCR8-targeting agents are identified and/or characterized as described herein in assays that detect direct binding of such agents to CCR8. In some embodiments, such direct binding is detected in vitro (e.g., with isolated CCR8 protein); in some embodiments, such direct binding is detected in or on cells (e.g., Treg cells); in some embodiments, such direct binding is detected in or on tissues (e.g., tumor tissues); in some embodiments, such direct binding is detected in or on an organism (e.g., a model organism, a non-human animal, or a human).

In some embodiments, useful CCR8-targeting agents as described herein are identified and characterized based on their ability to detectably bind to cells that express CCR8, and particularly to deplete Treg cells, especially tumor-infiltrating Treg cells.

In some embodiments, useful CCR8-targeting agents as described herein are identified and characterized based on their ability to deplete (e.g., to inhibit proliferation of and/or to kill) cells that express CCR8, and particularly to deplete Treg cells, especially tumor-infiltrating Treg cells.

Those skilled in the art will be aware of a variety of appropriate assay formats for assessing specific binding to CCR8 and/or detection and/or depletion of CCR8-expressing cells as described herein (see, for example, MAbs. 2012 July-August; 4(4):445-57; Immunol Rev. 2008 April; 222: 9-27).

As will be apparent to those skilled in the art, useful assays for identifying and/or characterizing agents that effectively deplete Treg cells, in some embodiments, can include assays that assess ADCC activity including, for example, as described in Clin Cancer Res. 2006 May 1; 12(9):2879-87.

In some embodiments, CCR8-targeting agents are identified and/or characterized via a process that involves providing a collection of test agents, contacting them with a CCR8-containing system (e.g., an in vitro system, a cellular system, a tissue system, and organism) under conditions that permit detection and/or quantification of binding by agents to CCR8 and/or depletion of tumor-infiltrating Treg cells. In some embodiments, such contacting is performed under conditions that, as will be understood by those skilled in the art, permit assessment of CCR8-specific binding and/or Treg depletion. In some embodiments, such contacting is performed under conditions that permit comparison with an appropriate reference such as, for example, a positive or negative control agent whose ability to bind specifically to CCR8 and/or to deplete tumor-infiltrating Treg cells is previously known.

Uses

The present disclosure provides data that show CCR8 to be selectively expressed on tumor infiltrating Treg cells as compared to effector T cells in the tumor as well as normal circulating T cells. These findings implicate CCR8 as a therapeutic target to eliminate, inhibit the migration or function of Treg cells, which can, among other things, augment (natural and/or pharmaceutically or otherwise enhanced) anti-tumor immune responses. Alternatively or additionally, these findings implicate CCR8 as a diagnostic target for detection and/or characterization of tumors infiltrated by Treg cells. In some embodiments, as will be appreciated by those skilled in the art reading the present disclosure, detection and/or characterization extent and/or nature of Treg infiltration can designate a tumor as likely (or not) to benefit from certain therapeutic interventions, including as described herein (e.g., a CCR8-targeting regimen and/or an immunotherapeutic regimen, as described herein). Alternatively or additionally, detection and/or characterization extent and/or nature of Treg infiltration can be used to monitor effectiveness of a particular therapeutic regimen (e.g., a CCR8-targeting regimen and/or an immunotherapeutic regimen, as described herein) against a particular tumor, e.g., in a specific subject. Thus, in various embodiments, the present invention provides both diagnostic and therapeutic technologies that involve detecting and/or targeting CCR8, and/or Treg cells that express it, in subjects with tumors.

Extensive preclinical data suggest that Treg cells represent a common mechanism of immune evasion across most malignancies. Thus, those skilled in the art, reading the present disclosure, will appreciate that CCR8-targeting strategies (e.g., Treg-detection and/or -depletion strategies as described herein are applicable across a wide range of malignancies).

In some embodiments, CCR8-targeting technologies as described herein are useful in the diagnosis and/or treatment of any of a variety of cancers. The Examples herein specifically demonstrate use of provided technologies with respect to breast cancer.

Excluding skin malignancies, breast cancer is the most common cancer among women and the second leading cause of cancer death in women (Ref 62). Clinically, pathologic evaluation of breast cancer specimens has revealed the prognostic value of certain histopathologic features of breast tumors that reflect alterations in the microenvironment including lymphocytic infiltration, fibrosis, and angiogenesis. While breast cancer has not traditionally been considered an immunogenic tumor, the present disclosure appreciates that evidence of tumor infiltrating lymphocytes (TILs) and their subset composition paralleling disease progression suggest that the immune response may be important(Refs: 63 and 64). The clinical relevance of tumor infiltrating T cells has been intensively studied(Ref: 65). An increased ratio of CD4+ to CD8+ T cells correlates with lymph node metastases and reduced overall survival(Ref: 66). The tumor microenvironment can also influence the recruitment and regulation of immune cells in breast tumors(Refs: 67 and 68). High levels of Treg cells in breast tumors is associated with an invasive phenotype and diminished relapse-free as well as overall survival(Refs: 69 and 71). In addition, a substantial decrease in the number of breast tumor infiltrating Treg cells is positively associated with a pathological response to neoadjuvant chemotherapy(Ref: 72). In accordance with the present invention, breast cancer is a particular cancer of interest for diagnosis and/or treatment with provided technologies.

Breast cancer is a heterogeneous disease and is generally classified into three basic therapeutic groups, based on the expression of the estrogen receptor (ER), progesterone receptor (PR), and HER2 (Ref: 73). Triple negative breast cancers (TNBC), also known as basal-like breast cancers, lack expression of ER, PR, and HER2 (Ref: 74). These tumors account for up to 15% of all invasive breast cancers and are frequently observed in patients with BRCA1 germline mutations and of African ancestry. TNBCs characteristically are densely infiltrated by lymphocytes suggestive of an anti-tumor response, yet are associated with a more aggressive clinical course characterized by shorter survival and higher risk of metastases(Ref: 75). This paradox is hypothesized to be secondary to effective immune suppression by the tumor microenvironment with preclinical data implicating Treg cells. Foxp3 expression among tumor infiltrating lymphocytes is significantly associated with the TNBC subtype of invasive breast cancers(Ref: 76). High levels of Treg cell infiltration of TNBCs is associated shorter survival(Ref: 77). According to the present invention, TNBC represents a relevant target for diagnosis and/or therapy with provided technologies. Moreover, TNBC represents a particularly relevant target for use of one or more immunotherapy modalities in combination with CCR8-targeted depletion technologies as described herein, given that there is a robust pre-existing infiltrate which can potentially mount an anti-tumor response once the Treg cell-mediated immunosuppression is diminished through CCR8-mediated Treg cell depletion.

Those skilled in the art, reading the present disclosure, will appreciate that association of Treg cell accumulation in the peripheral blood and tumor infiltrating lymphocytes with clinical outcome is not limited to patients with breast cancer. As Treg cells represent a central mechanism of tumor immune evasion, robust tumor infiltration by Treg cells correlates with poor survival in patients affected by many tumor types. Gastric cancer represents one of the most common causes of cancer-related deaths worldwide(Ref: 78). In metastatic gastric cancer, chemotherapy remains the mainstay of therapy and results in objective response rates of only 20-40%, with a median overall survival of 8-10 months (Ref: 79). This particularly grim prognosis has led to the investigation of immunotherapy as a means to improve survival(Ref: 80). Promising results from initial trials suggest that gastric cancer may be amenable to treatment by modulating the immune system. A clinical trial investigating the use of autologous cytokine-induced killer cells for locally advanced gastric cancer patients showed significant improvements in disease-free and overall survival(Ref: 81). A significant amount of preclinical data also suggests that targeting Treg cells in gastric cancer holds therapeutic promise. A study of 133 patients with gastric cancer revealed that high numbers of intratumoral Treg cells significantly correlated presence of lymph node metastases and was an independent factor for adverse overall survival(Ref: 82). Regulatory T cells from patients with gastric cancer have also been shown to produce the immunosuppressive cytokines IL-4 and IL-10, and inhibit cytokine production from CD4+ T cells in vitro(Ref: 83). Treg cell infiltration of gastric cancers may be in part related to hypoxia, a feature common to many solid tumors. Treg cell infiltration into gastric cancers is positively correlated with HIF-1α expression and supernatants from gastric cancer cells cultured in hypoxic conditions can induce the expression of Foxp3 in naïve CD4+ T cells via TGF-β1 (Ref: 84). In accordance with the present invention, gastric cancer is a target cancer of particular interest for diagnosis and/or therapy with CCR8-targeted technologies as provided herein. Moreover, in some embodiments, gastric cancer is a cancer of particular interest for use of provided CCR8-targeted technologies in combination with one or more other immunotherapy modalities.

Lung cancer is also a target cancer of particular interest for application of provided technologies. Lung cancer is the leading cause of cancer deaths worldwide. The overall 5-year survival rate for advanced non-small cell lung cancer (NSCLC) is 2%-4%, depending on geographic location(Ref: 85). Whereas renal cell carcinoma and melanoma are traditionally considered immunogenic, as evidenced by spontaneous regressions and occasional dramatic responses to high-dose IL-2, NSCLC has been notoriously resistant to immunotherapy(Refs 86 and 87). Pre-clinical data suggest that the immune system may have a role in this disease. High levels of $CD4^+/CD8^+$ T cells infiltrating resected NSCLC tumors are associated with a favorable prognosis and high levels of infiltrating Treg cells are associated with increased risk of relapse(Refs 88 and 89). In early-stage NSCLC the ratio of Treg cells to CD3+ TILs correlates with disease specific survival and can reliably distinguish patients with tumors who are at high risk for recurrence(Refs 90 and 91). Genetic evidence pointing to the role of Treg cells in the risk of developing NSCLC was documented by determining the presence of a single nucleotide polymorphism (SNP) associated with Graves disease in a cohort of patients with NSCLC and healthy controls. The study demonstrated a significant association of this SNP with a risk of developing NSCLC(Ref 92). Recently there have been significant breakthroughs in harnessing the immune system through the use of checkpoint blockade inhibitory antibodies to treat NSCLC. In a Phase I dose escalation study of 207 patients treated with an anti-PD-L1 monoclonal antibody, a response rate of 10% was observed in patients with NSCLC (Ref 93). Another Phase I dose-escalation study of 296 patients treated with an anti-PD-1 antibody reported a response rate of 18% in patients with NSCLC(Ref 94). The present disclosure provides the insight that the association of Treg cells with the clinical course of NSCLC patients as well as the significant pool of proof-of-principle clinical data that immune modulation can yield therapeutic responses in this disease, depleting Treg cells is a promising therapeutic modality for lung cancer patients, and particularly for NSCLC patients. Moreover, in some embodiments, lung cancer, including specifically NSCLC, is a cancer of particular interest for use of provided CCR8-targeted technologies in combination with one or more other immunotherapy modalities.

Combination

The present invention appreciates that, in many embodiments, provided diagnostic and/or therapeutic compositions and/or strategies that target CCR8 (e.g., by utilizing CCR8-targeting agents) may be combined with one or more other therapeutic and/or diagnostic modalities useful in the treatment of cancer. Those skilled in the art will be well aware of approved or otherwise appropriate such modalities, taking into consideration the type of cancer involved in any particular instance, and/or the nature, characteristics, and/or history of the relevant subject.

In some embodiments, provided CCR8-targeting strategies are combined with forms of treatment including but not limited to pharmacotherapy, chemotherapy, mesotherapy, medical devices, surgery, gene therapy, hormone therapy, radiotherapy, phototherapy, electrotherapy, thermotherapy, and cryotherapy. In some embodiments, provided CCR8 targeting strategies are combined with biologics, cells, proteins, steroids, hormones, cytokines, enzymes, peptides, polypeptides, amino acids, nucleic acids, DNA, RNA, mRNA, tRNA, siRNA, dsRNA, DNA vaccines, antibodies, monoclonal antibodies, polyclonal antibodies, antibody-drug conjugates, antivirals, antibiotics, antifungals and any conjugates thereof.

In some embodiments, provided CCR8 targeting strategies are combined with anti-inflammatory agents to treat cancer. Anti-inflammatory agents include both steroids and non-steroidal anti-inflammatory drugs (NSAID). In some embodiments, provided CCR8 targeting strategies are combined with steroids, including but not limited to glucocorticoids and corticosteroids. In some embodiments, provided CCR8 targeting strategies are combined with non-steroidal anti-inflammatory drugs, including but not limited to ibuprofen, aspirin, naproxen sodium, celecoxib, sulindac, oxaprozin, salsalate, diflunisal, piroxicam, indomethacin, etodolac, meloxicam, naproxen, nabumetone, tromethamine, diclofenac, esomeprazole, and acetaminophen.

In some embodiments, provided CCR8 targeting strategies are combined with medical imaging modalities to treat and/or monitor cancer. In some embodiments, provided CCR8 targeting strategies are combined with medical imaging modalities including but not limited to echocardiography, thermography, tomography, photoacoustic imaging, ultrasound, magnetic resonance imaging, nuclear medicine, elastography, positron emission tomography, computed tomography, and fluorescence tomography.

In some embodiments, CCR8 targeting strategies as described herein are combined with other strategies that also specifically target Treg cells, and particularly with strategies that specifically target tumor-infiltrating Treg cells. For example, in some particular embodiments, diagnostic and/or therapeutic compositions and/or strategies utilizing CCR8-targeting agents may be combined with one or more other therapeutic and/or diagnostic modalities that also target Tregs for depletion (as reviewed, for example, in Pere et al, Oncoimmunology 1(3):326, 2012-05-01).

To give but a few examples, certain chemotherapeutic regimens are thought to reduce Treg by promoting dendritic cell maturation (see, for example, Zitvogel et al Nat Rev Clin Oncol. 8:151, 2011). Alternatively or additionally, modalities that destroy proliferating cells, may shift the balance of T cells in tumor environments toward T effector cells as compared with Tregs. In some embodiments, metronomic dosing of such anti-proliferative agents may achieve selective reduction of Treg populations (see for example Polak & Turk Nature. 249:654, 1974; Ercolini et al J Exp Med. 201:1591, 2005; Chen et al. Mol Ther. 18:1233, 2010).

Alternatively or additionally, in some embodiments, the present invention contemplates combination of provided diagnostic and/or therapeutic compositions and/or strategies utilizing CCR8-targeting with one or more other modalities that also targets a Treg-associated marker or markers. Representative such markers include for example, CD25, CTLA-5. GITR. OX40, one or more TLR ligands (e.g., TLR4, TLR5, TLR7, and/or TLR8), CD39, CD73, Foxp3, CCL17, CCR4, CCL22, CCR7, and/or CCR5.

CTLA-4 is expressed on both regulatory and activated T cells, and anti-CTLA-4 strategies have been proposed as potential approaches for depleting Treg cells or otherwise improving and/or promoting anti-tumor immune reactions (see, for example, Peggs et al J Exp Med 206:1717, 2009).

GITR is constitutively expressed by Treg and is also detected, albeit at lower levels, on $CD4^+$ and $CD8^+$ effector T cells. Agonistic antibodies to either GITR or GITR ligand have been reported to 1) suppress Treg activity; 2) enhance proliferation of effector T cells; and 3) improve effector cells' ability to resist Treg-mediated suppression (see, for example, Turk et al J Exp Med 200:771, 2004; Ko et al J Exp Med. 202:885, 2005; Stephens et al J Immunol. 173:5008, 2004).

OX40 is a costimulatory molecule of the TNF receptor family that is constitutively expressed on Treg and transiently expressed on activated effector T cells. Use of agnostic anti-OX40 antibodies has been reported to inhibit Treg suppressive activity, and to reduce tumor growth (Valzasina et al Blood. 105:2845, 2005; Piconese et al. J Exp Med. 205:825, 2008).)

Various TLRs (including specifically TLR4, TLR5, TLR7 and TLR8) are expressed bt Treg cells, and activation of at least TLR 8 has been shown to inhibit Treg function and enhance in vivo tumor immunity (Peng et al Science. 309:1380, 2005).

Treg numbers and/or function can also be suppressed by inhibiting catabolism of adenine nucleotides (ATP, ADP and AMP) by extracellular ectonucleotidases, CD39 and CD73, for example through use of adenosine inhibitors and/or adenosine receptor antagonists (Blackburn et al Handb Exp Pharmacol. 215, 2009). Inhibition of CD39 with enzymatic inhibitors has been reported to Treg function and improve certaom effects of chemotherapy (Michaud et al Science. 334:1573, 2011).

Inhibition of Foxp3 has been reported to impair Treg activity (Casares et al. J Immunol. 185:5150, 2010), and may in some embodiments be useful in accordance with the present invention.

Another strategy to inhibit and/or deplete Tregs, for example in combination with inventive strategies as described herein, is to target chemokine/chemokine receptor molecules (e.g., CCL17/CCL22-CCR4 axis) that are involved in Treg trafficking and/or in T cell suppression of effector cell activity. Tumor cells and their microenvironment attract Treg by the secretion of CCL22 (22), and a correlation has been reported between the presence of tumor-infiltrating Treg and CCL22 in breast cancer (Gobert et al Cancer Res. 69:2000, 2009). In a murine model, it has been shown that monoclonal antibodies specific for CCL22 significantly reduce the migration of Treg into ovarian tumors (Curiel et al Nat Med. 10:942, 2004). Recently, small molecule antagonists of CCR4 have been shown to prevent the interaction of CCL22/CCL17 with their receptor and to inhibit the recruitment of Treg mediated by CCL22 and CCL17. The present disclosure specifically demonstrates expression of CCR4 in tumor-infiltrating Tregs; in some embodiments, CCR8 and CCR4 are targeted in combination (e.g., simultaneously).

Other chemokine receptors such as CCR7 and CCR5 may also play a role in Treg migration; administration of a CCR5 inhibitor has been reported to reduce Treg migration into tumors, and to increase effectiveness of immunotherapy in reducing tumors (see, for example, Tan et al. J Immunol. 182:1746, 2009; Conforti et al. Cancer Res. 70:490, 2010).

In some particular embodiments, diagnostic and/or therapeutic compositions and/or strategies utilizing CCR8-targeting agents may be combined with one or more other therapeutic and/or diagnostic modalities that inhibit angiogenesis.

In some particular embodiments, diagnostic and/or therapeutic compositions and/or strategies utilizing CCR8-targeting agents may be combined with one or more other therapeutic and/or diagnostic modalities that target one or more tyrosine kinases. For example, it has been demonstrates that in both mouse and human gastrointestinal carcinomas, use of tyrosine kinase inhibitors (e.g., imatinib mesylate, dasatinib, temozolomide, etc) can reduce Treg cell numbers in tumors, resulting in increased Natural Killer (NK) cell functions effective against them (see, for example, Balachandran et al Nat Med. 17:1094, 2011; Banissi et al Cancer Immunol Immunother. 58:1627, 2009; Delahaye et al. Nat Med. 17:700, 2011).

In some particular embodiments that involve combination targeting of two or more markers such as, for example, two or more Treg-associated markers, the present invention contemplates use of multifunctional targeting agents as are known in the art such as, for example, multi-functional antibody formats including but not limited to multifunctional (e.g., bifunctional antibodies, zybodies, glycoengineered antibodies, etc).

The present disclosure appreciates that accumulating evidence demonstrates that Treg cells utilize components of the specific immune response in which they are acting to suppress the immune response itself. For example, expression of the transcription factor Irf4 is required for Tregs to be able to suppress TH2 responses, and Irf4 controls a module of the Foxp3 program that contains 20% of its targets (Ref. 15). Similarly CXCR3, a target of Tbet, is required for control of TH1 responses (Ref. 16), and Stat3 for TH17 responses (Ref. 17). Without wishing to be bound by any particular theory, the present disclosure observes that observations suggest that Tregs integrate external local cues to modulate specific segments of their transcriptomic program, and furthermore that they do so by a set of common regulators they share with the ongoing immune response.

The present disclosure further provides the insight that, because Treg cells may be critical mediators of the immunosuppressive microenvironment, depleting or ablating Treg as described herein may convert tumor subtypes classically considered "non-immunogenic" to a state where immune intervention is possible. The present invention therefore specifically teaches, in some embodiments, the treatment of cancer by depletion of Treg cells (e.g., through use of CCR8-targeting agents as described herein) in combination with one or more immunomodulatory modalities of cancer therapy such as, for example, antibody blockage of inhibitory molecules, adoptive T cell transfer, and/or vaccination or other strategies. In some embodiments of the present invention, CCR8-targeting is combined with one or more such strategies to detect, characterize, and/or treat cancer.

The present disclosure specifically contemplates combination of provided CCR8-targeting technologies with ionizing radiation therapy. Ionizing radiation therapy is widely used for the management of certain cancers, particularly including breast cancer, and its advantages derive from its ability to induce cell death and proliferation arrest, depending on the context. More recently, it has been suggested that radiotherapy has the added benefit of immune modulation (see, for example, Formenti et al Lancet Onc. 10:718, July 2009) contributing to enhanced antigen and danger signal release from dying cancer cells and antigen presentation from dendritic cells, as well as down-regulating antigens upon reduction of tumor mass, which reduces the chances of tolerance induction. Specific rational for a combinatorial approach with Treg ablation as described herein is the known relative radio-resistance of Treg cells, discovered when exploring the reasons behind the inability to transmit disease through scurfy bone marrow transfer into lethally irradiated hosts (see, for example, Komatsu et al Proc. Natl. Acad. Sci USA 104:8959, May 22, 2007. Current clinical outcomes might be significantly improved by combination of Treg depletion strategies with radiation, and possibly chemotherapy or targeted therapies against molecular drivers of oncogenesis.

Pharmaceutical Compositions

In some embodiments, the present invention provides pharmaceutical compositions comprising one or more provided agents (e.g., CCR-8 targeting agents) together with one or more pharmaceutically acceptable excipients.

In some embodiments, provided pharmaceutical compositions may be prepared by any appropriate method, for example as known or hereafter developed in the art of pharmacology. In general, such preparatory methods include the step of bringing a provided CCR8 targeting agent into association with one or more pharmaceutically acceptable excipients, and then, if necessary and/or desirable, shaping and/or packaging the product into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of the pharmaceutical composition comprising a predetermined amount of one or more provided CCR8 targeting agent. The amount of the provided CCR8 targeting agent is generally equal to the dosage of the provided CCR8 targeting agent which would be administered to a subject and/or a convenient fraction of such a dosage such as, for example, one-half or one-third of such a dosage.

In some embodiments, provided pharmaceutical compositions are specifically formulated for mucosal delivery (e.g., oral, nasal, rectal or sublingual delivery). In some embodiments, pharmaceutical compositions are specifically formulated for oral delivery as being conjugated to starch and mixed with food.

In some embodiments, appropriate excipients for use in provided pharmaceutical compositions may, for example, include one or more pharmaceutically acceptable solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. Alternatively or additionally, pharmaceutically acceptable excipients such as cocoa butter and/or suppository waxes, coloring agents, coating agents, sweetening, flavoring, and/or perfuming agents can be utilized. Remington's *The Science and Practice of Pharmacy*, $21^{st}$ Edition, A. R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, liquid dosage forms (e.g., for oral and/or parenteral administration) include, but are not limited to, emulsions, microemulsions, solutions, suspensions, syrups, and/or elixirs. In addition to provided CCR8 targeting agent(s), liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR, alcohols, oils, modified oils, glycols, polysorbates, cyclodextrins, polymers, and/or combinations thereof.

In some embodiments, injectable preparations, for example, sterile aqueous or oleaginous suspensions, may be formulated according to known methods using suitable dispersing agents, wetting agents, and/or suspending agents. Sterile liquid preparations may be, for example, solutions, suspensions, and/or emulsions in nontoxic parenterally acceptable diluents and/or solvents, for example, as a solution in 1,3-butanediol. Among the acceptable vehicles and solvents that may be employed, for example, are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of liquid formulations.

Liquid formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, one or more strategies may be utilized prolong and/or delay the effect of a provided CCR8 targeting agent after delivery.

In some embodiments, provided pharmaceutical compositions may be formulated as suppositories, for example for rectal or vaginal delivery. In some embodiments, suppository formulations can be prepared by mixing utilizing suitable non-irritating excipients such as cocoa butter, polyethylene glycol or a suppository wax which are solid at ambient temperature but liquid at body temperature and therefore melt in the body (e.g., in the rectum or vaginal cavity) and release the provided CCR8 targeting agent.

In some embodiments, solid dosage forms (e.g., for oral administration) include capsules, tablets, pills, powders, and/or granules. In such solid dosage forms, the provided CCR8 targeting agent(s) may be mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

In some embodiments, solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Exemplary enteric coatings include, but are not limited to, one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); HP55; polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac, and combinations thereof.

In some embodiments, solid dosage forms may optionally comprise opacifying agents and can be of a composition that they release the provided CCR8 targeting agent(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In some embodiments, the present invention provides compositions for topical and/or transdermal delivery, e.g., as a cream, liniment, ointment, oil, foam, spray, lotion, liquid, powder, thickening lotion, or gel. Particular exemplary such formulations may be prepared, for example, as products such as skin softeners, nutritional lotion type emulsions, cleansing lotions, cleansing creams, skin milks, emollient lotions, massage creams, emollient creams, make-up bases, lipsticks, facial packs or facial gels, cleaner formulations such as shampoos, rinses, body cleansers, hair-tonics, or soaps, or dermatological compositions such as lotions, ointments, gels, creams, liniments, patches, deodorants, or sprays.

In some embodiments, provided compositions are stable for extended periods of time, such as 1 week, 2 weeks, 1 month, 2 months, 6 months, 1 year, 2 years, 3 years, or more. In some embodiments, provided compositions are easily transportable and may even be sent via traditional courier or other package delivery service. Accordingly, some embodiments may be useful in situations of disease outbreak, such as epidemics, or attacks with biological agents at least in part due to their ability to be stored for long periods of time and transported quickly, easily, and safely. Such attributes may allow for rapid distribution of provided compositions to those in need.

In some embodiments, it may be advantageous to release CCR8 targeting agent(s), at various locations along a subject's gastrointestinal (GI) tract. In some embodiments, it may be advantageous to release CCR8 targeting agent(s), for example, an agent, in a subject's mouth as well as one or more locations along the subject's GI tract. In some embodiments, it may be advantageous to release CCR8 targeting agent(s), for example, an agent, in a subject's GI tract, including but not limited to the stomach, intestines, and colon. Accordingly, in some embodiments, a plurality of provided compositions (e.g., two or more) may be administered to a single subject to facilitate release of CCR8 targeting agent(s) at multiple locations. In some embodiments, each of the plurality of compositions has a different release profile, such as provided by various enteric coatings, for example. In some embodiments, each of the plurality of compositions has a similar release profile. In some embodiments, the plurality of compositions comprises one or more CCR8 targeting agents. In some embodiments, each of the plurality of administered compositions comprises a different CCR8 targeting agent. In some embodiments, each of the plurality of compositions comprises the same CCR8 targeting agent.

Dosing

It is contemplated that any of a variety of dosing regimens may be used in accordance with various embodiments. In some embodiments, the step of stimulating comprises administering at least two doses of a CCR8 targeting agent, separated by a period of time. In some embodiments, the step of stimulating comprises administering at least three, four, five, six or more than six doses of a CCR8 targeting agent, each separated by a period of time. In some embodiments, the period of time between each administration is the same. In some embodiments, the period of time between each administration is different. In some embodiments, the period of time between doses may be 1 minute, 15 minutes, 30 minutes, 1 hour, 2 hours, 3 hours, 6 hours, 12 hours, 24 hours, 48 hours, 72 hours, 96 hours, 1 week, 2 weeks, or 1 month. In some embodiments, the period of time between doses is greater than 1 month. In some embodiments, each dose is administered substantially simultaneously (e.g., sequentially).

According to various embodiments comprising administration of two or more doses of a CCR8 targeting agent, the dose of CCR8 targeting agent may vary according to sound medical judgment. In some embodiments, each dose of a CCR8 targeting agent is the same. In some embodiments, each dose of a CCR8 targeting agent may vary from one or more other doses.

In some embodiments, a CCR8 targeting agent is administered at a dose equal to or approximating a therapeutically effective amount. In some embodiments, a therapeutically effective amount of a CCR8 targeting agent may be an amount ranging from about 0.001 to about 1,000 mg/kg. In some embodiments, a therapeutically effective amount may be, for example, about 0.001 to 500 mg/kg weight, e.g., from about 0.001 to 400 mg/kg weight, from about 0.001 to 300 mg/kg weight, from about 0.001 to 200 mg/kg weight, from about 0.001 to 100 mg/kg weight, from about 0.001 to 90 mg/kg weight, from about 0.001 to 80 mg/kg weight, from about 0.001 to 70 mg/kg weight, from about 0.001 to 60 mg/kg weight, from about 0.001 to 50 mg/kg weight, from about 0.001 to 40 mg/kg weight, from about 0.001 to 30 mg/kg weight, from about 0.001 to 25 mg/kg weight, from about 0.001 to 20 mg/kg weight, from about 0.001 to 15 mg/kg weight, from about 0.001 to 10 mg/kg weight. In some embodiments, the therapeutically effective amount described herein is provided in one dose. In some embodiments, the therapeutically effective amount described herein is provided in one day.

In some embodiments, a therapeutically effective dosage amount may be, for example, about 0.0001 to about 0.1 mg/kg weight, e.g. from about 0.0001 to 0.09 mg/kg weight, from about 0.0001 to 0.08 mg/kg weight, from about 0.0001 to 0.07 mg/kg weight, from about 0.0001 to 0.06 mg/kg weight, from about 0.0001 to 0.05 mg/kg weight, from about 0.0001 to 0.04 mg/kg weight, from about 0.0001 to 0.03 mg/kg weight, from about 0.0001 to 0.02 mg/kg weight, from about 0.0001 to 0.019 mg/kg weight, from about 0.0001 to 0.018 mg/kg weight, from about 0.0001 to 0.017 mg/kg weight, from about 0.0001 to 0.016 mg/kg weight, from about 0.0001 to 0.015 mg/kg weight, from about 0.0001 to 0.014 mg/kg weight, from about 0.0001 to 0.013 mg/kg weight, from about 0.0001 to 0.012 mg/kg weight, from about 0.0001 to 0.011 mg/kg weight, from about 0.0001 to 0.01 mg/kg weight, from about 0.0001 to 0.009 mg/kg weight, from about 0.0001 to 0.008 mg/kg weight, from about 0.0001 to 0.007 mg/kg weight, from about 0.0001 to 0.006 mg/kg weight, from about 0.0001 to 0.005 mg/kg weight, from about 0.0001 to 0.004 mg/kg weight, from about 0.0001 to 0.003 mg/kg weight, from about 0.0001 to 0.002 mg/kg weight. The effective dose for a particular individual can be varied (e.g., increased or decreased) over time, depending on the needs of the individual.

Routes of Administration

In some embodiments, provided CCR8 targeting agents and compositions comprising the same may be formulated for any appropriate route of delivery. In some embodiments, provided CCR8 targeting agents and compositions comprising the same may be formulated for any route of delivery, including, but not limited to, bronchial instillation, and/or inhalation; buccal, enteral, interdermal, intra-arterial (IA), intradermal, intragastric (IG), intramedullary, intramuscular (IM), intranasal, intraperitoneal (IP), intrathecal, intratracheal instillation (by), intravenous (IV), intraventricular, mucosal, nasal spray, and/or aerosol, oral (PO), as an oral spray, rectal (PR), subcutaneous (SQ), sublingual; topical and/or transdermal (e.g., by lotions, creams, liniments, ointments, powders, gels, drops, etc.), transdermal, vaginal, vitreal, and/or through a portal vein catheter; and/or combinations thereof. In some embodiments, the present invention provides methods of administration of CCR8 targeting agents and compositions comprising the same via mucosal administration. In some embodiments, the present invention provides methods of administration of CCR8 targeting agents and compositions comprising the same via oral administration.

In some embodiments, provided CCR8 targeting agents and compositions comprising the same may be formulated for oral delivery. In some embodiments, provided CCR8 targeting agents and compositions comprising the same may be formulated for topical delivery.

Kits

In some embodiments, the present invention further provides kits or other articles of manufacture which contain one or more CCR8 targeting agents or formulations containing the same, and provides instructions for its reconstitution (if lyophilized) and/or use. In some embodiments, a kit may comprise (i) at least one provided CCR8 targeting agent or composition comprising the same; and (ii) at least one pharmaceutically acceptable excipient; and, optionally, (iii) instructions for use.

Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration.

In some embodiments, a container may contain a single dose of a stable formulation containing one or more CCR8 targeting agents. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline).

Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml).

Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

In some embodiments, kits include multiple (e.g., 1, 2, 3, 4, 5, 6, 7, 8, 9, 10, 11, 12, 13, 14, 15, 16, 17, 18, 19, 20, or more) doses of provided CCR8 targeting agents and/or compositions comprising the same. In some embodiments, kits include multiple (e.g., 1, 2, 3, 4, 5, 6, 7, 8, 9, 10, 11, 12, 13, 14, 15, 16, 17, 18, 19, 20, or more) populations of provided CCR8 targeting agents and/or compositions comprising the same having different functional elements (e.g., CCR8 targeting agents). In some embodiments, multiple populations of provided CCR8 targeting agents and/or compositions comprising the same are packaged separately from one another in provided kits. In some embodiments, provided kits may include provided compositions and one or more other therapeutic agents intended for administration with the provided compositions.

EXAMPLES

Example 1. Targeting CCR8 to Specifically Deplete Tumor-Infiltrating Tregs

The present Example describes identification of CCR8 as a specific marker of tumor infiltrating Tregs and as a target against which therapeutic strategies (e.g., depleting antibodies, can and should be directed). Specifically, the present Example demonstrates that CCR8 is specifically expressed in tumor-infiltrating Tregs as compared with other tumor infiltrating T cell subsets (i.e., CD4 and CD8 T cells).

Among other things, the present work identifies the source of a problem in certain prior efforts to identify and/or characterize differentially expressed targetable genes in tumor-associated immune cell subsets. Specifically, the present work appreciates that, in the tumor microenvironment, not only does immune cell composition vary from tumor to tumor (Ref: 42), but each cell type within a tumor depends on interactions with other cells for its recruitment, survival, or function. Large-scale studies that collect genomic or transcriptomic data from total tissue produce variable data that is difficult to interpret without considering the microenvironmental context. In silico dissection of mixed cell samples using raw data has been utilized to deconvolve expression data, but underdetection of gene expression signatures and their relative functional contribution is still a major problem (Ref: 43).

We isolated Treg cells, effector CD4 T cells and CD8 T cells from breast infiltrating duct carcinomas as well as normal breast parenchyma and peripheral blood for in depth transcriptome analysis by RNAseq.

Figure 4:
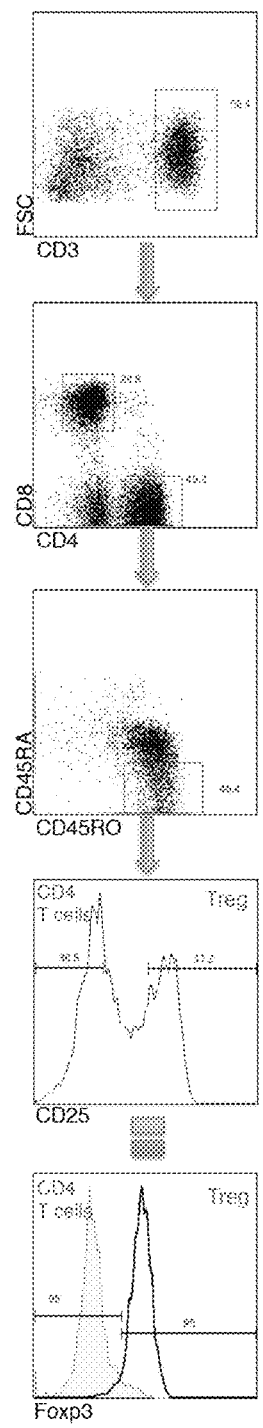
FIG. 4.

Tumor as well as corresponding normal tissue taken far from the primary tumor, or from contralateral prophylactic mastectomies, was harvested by the tumor Procurement Service (TPS) at Memorial Sloan Kettering Cancer Center. Tumor and normal tissue were cut in fine pieces and transferred to a 40 µm nylon mesh cell strainer immersed in 5 ml PBS buffer in a Petri dish. The tissue was be gently mashed with the end of a plunger to create a single cell suspension. A second filtration through a 40 µm nylon mesh was carried out. This procedure was repeated as necessary or desirable to wash the filters utilized and obtain maximal recovery. Cells were pelleted by spinning at 1000 rpm for 10 minutes at 4° C. Supernatant was aspirated carefully and a second wash was performed. The cell pellet resulting from this procedure was resuspended and stained with fluorescent antibodies for analysis by flow cytometry. Human Tregs were defined as $CD3^+CD4^+CD45RA^-CD45RO^+CD25^+$ (>95% $Foxp3^+$, FIG. 4); effector $CD4^+$ cells were defined as $CD3^+CD4^+CD45RA^-CD45RO^+CD25^->95\%$ $Foxp3^-$, FIG. 4), and effector $CD8^+$ T cells were defined as $CD3^+CD8^+$. Fluorescence-activated cell sorting (FACS) was used to obtain pure populations of these TIL subsets. Cells were sorted into Trizol LS™, and were stored at −80° C. until RNA extraction.

From the isolated cells, total RNA was extracted using Trizol LS™ reagent. cDNA was generated from 3 ng of rRNA depleted RNA using the SMARTer Universal Low Input Kit (Clontech) according to manufactures guidelines. First strand synthesis was initiated by a 5'-modified random hexamer utilizing reverse transcriptase with terminal transferase activity resulting in the addition of a few additional nucleotides at the 3' end of the newly synthesized cDNA. The newly-formed cDNA overhang base paired with the SMARTer oligonucleotide, thus creating an extended template for the RT and yielding modified cDNA fragments. Subsequent second strand synthesis and cDNA amplification were driven from the universal priming sites thus generating an unbiased cDNA population.

After ribogreen quantification and quality control of Agilent BioAnalyzer (RIN>7), resulting cDNA was sheared using the Covaris to achieve fragments in the range of 200 bp. Fragmented sample quality and yield were evaluated using Agilent BioAnalyzer. Fragmented material was used for library preparation according to the Ion ChIP-Seq Kit starting with the end-repair process (Life Technologies), with 12 to 16 cycles of PCR. The resulting barcoded samples were loaded onto template-positive Ion PI™ Ion Sphere™ Particles (ISPs) using the Ion One Touch system II and Ion PI™ Template OT2 200kit v2 Kit (Life Technologies). Enriched particles were sequenced on a Proton sequencing system using the 200 bp version 2 chemistry. On average of 70 to 80 million reads were generated per samples. The sequence data were processed and analyzed with the assistance of the Bioinformatics core facility at the Sloan Kettering Institute.

Figure 5:
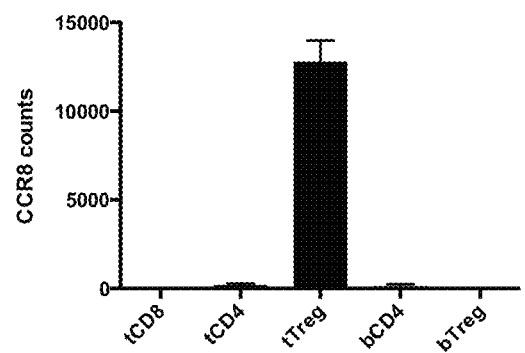
FIG. 5.

Our initial RNAseq data reveled CCR8 to be highly expressed in tumor infiltrating Treg and minimally expressed on other immune cells infiltrating the tumor (FIG. 5). In addition there was is very little expression of CCR8 on circulating blood Treg cells.

Figure 6:
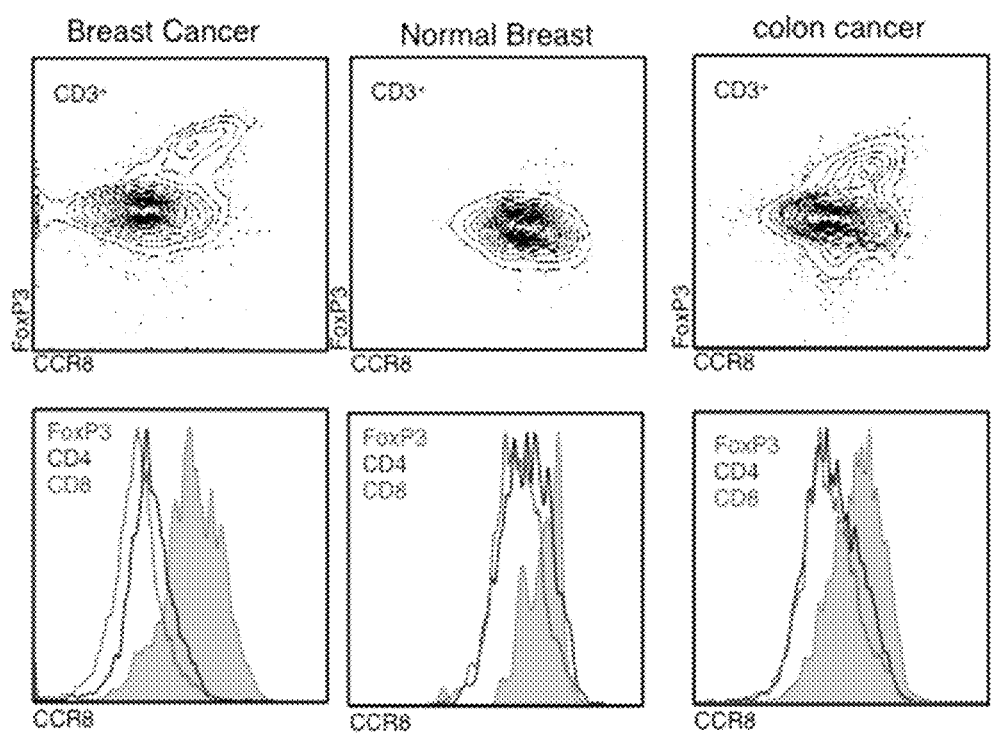
FIG. 6.

We confirmed the mRNA expression patterns of CCR8 by measuring CCR8 expression on the protein level by flow cytometry (FIG. 6). We found CCR8 to be preferentially expressed on Treg cells infiltrating human breast and colon cancer. In addition there was less of a differential expression pattern observed in normal tissue infiltrating T cells. Similarly there was little expression of CCR8 on circulating normal blood T cells. We therefore defined CCR8 as a useful target for depleting tumor-infiltrating Treg cells.

Figure 7:
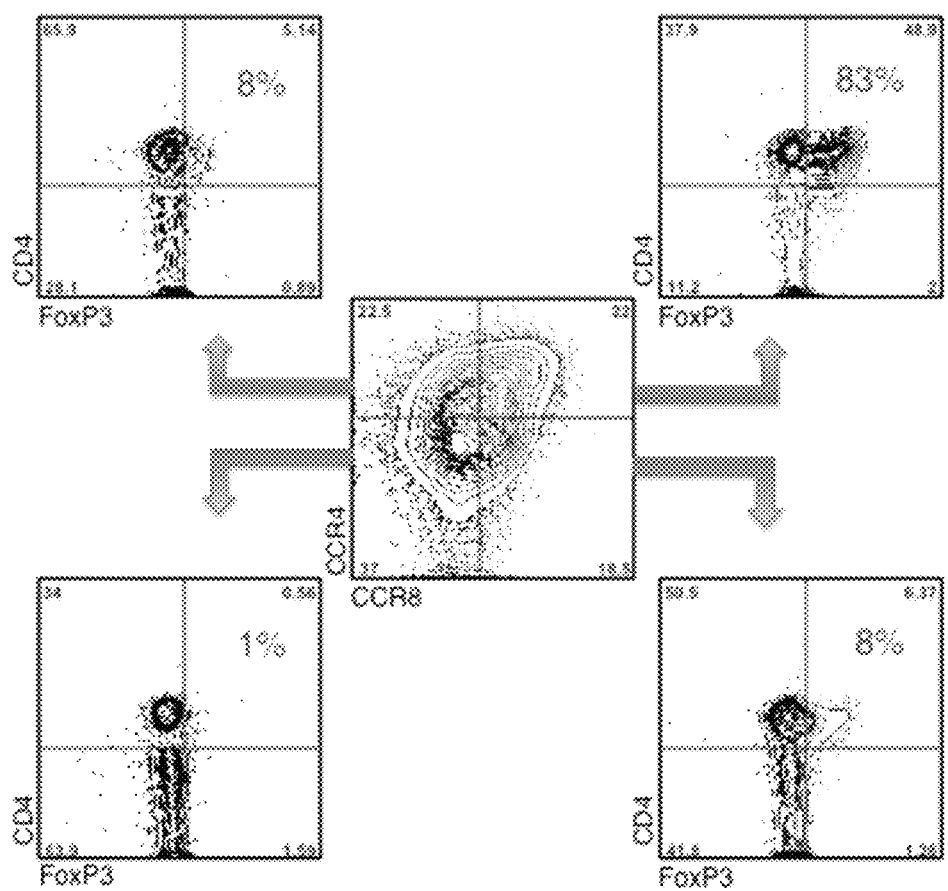
FIG. 7.

Furthermore, we found that there was significant overlap in expression of CCR4 and CCR8 expression on tumor infiltrating Treg cells, yet there were also Treg cells that expressed either chemokine receptor alone (FIG. 7). In some embodiments, the present disclosure contemplates a combination strategy in which both CCR8 and CCR4 are targeted to deplete tumor infiltrating Treg cells Such a strategy, in accordance with the present invention, would be able to effectively target 99% of tumor infiltrating Treg cells.

Example 2: Initial Studies Targeting Other Tree Surface Markers

The present Example describes initial studies targeting other markers present on the surface of Treg cells.

CTLA-4, PD-1 and its ligand PD-L1, like CCR8, are present in large amounts on the surface of Treg cells (21). Recently, CTLA-4 and PD-1/PD-L1 antibody-mediated blockade have been proven a viable immunotherapeutic strategy to treat solid tumors in pre-clinical and clinical settings.

The present Example describes studies to test whether combination with CTLA-4 or PD-1 checkpoint blockade might enhance the therapeutic effect of Treg cell ablation in our oncogene-driven breast cancer model. Blockade of either one of these pathways by CTLA-4 or PD-1 or PD-L1 or a combination of PD-1 and PD-L1 antibodies had no significant effect on the growth of PyMT-driven orthotopic tumors (data not shown). These results suggest that efficient targeting of Treg cells is necessary and sufficient to achieve an effective immunotherapeutic response to the growing tumor in this model of oncogene-dependent cancer.

Example 3: Confirmation of CCR8 Expression on Tumor Infiltrating Tregs

The present Example further documents the role of CCR8 expression on tumor infiltrating Tregs. For example, the present Example documents effects of CCR8 Treg expression on tumor volume, metastases, and proliferation.

Figure 8:
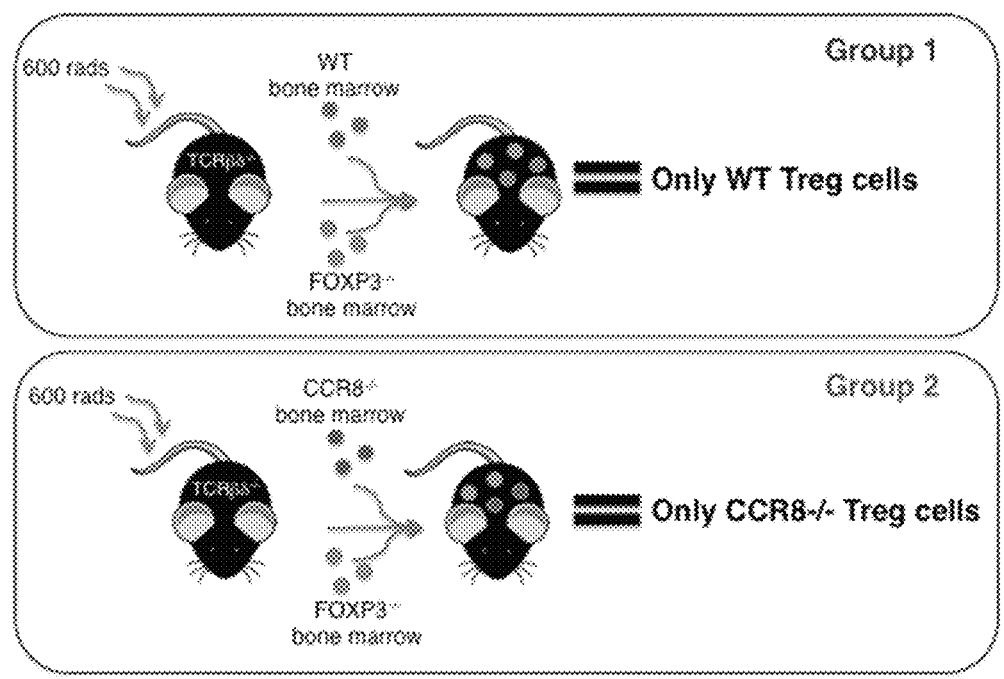
FIG. 8.
Figure 9:
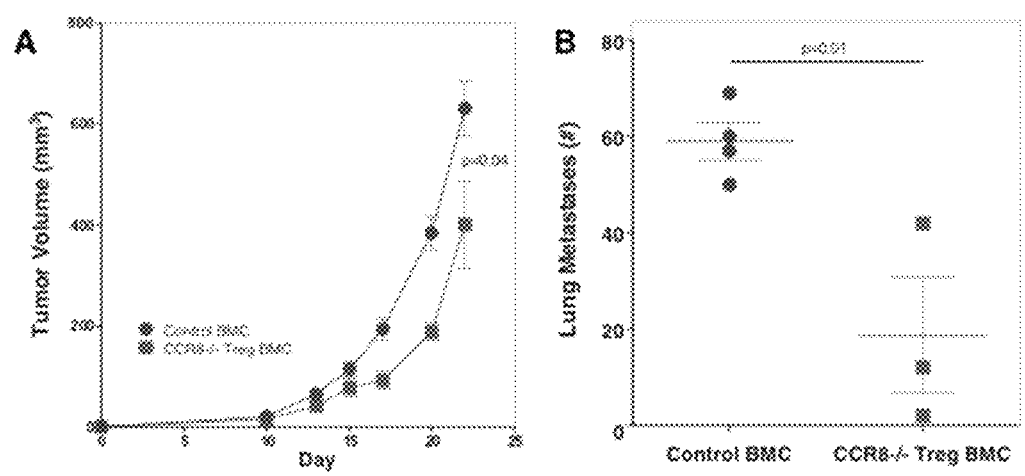
FIG. 9, Panels A-B.

The consequence of CCR8 expression on tumor infiltrating Treg cells was examined using a mixed bone marrow chimera experimental strategy (FIG. 8). With this approach we were able to develop two groups of mice, one with normal Treg cells and another with CCR8 deficient Treg cells. Carcinoma cells from C57BL/6 mice expressing a transgene encoding the PyMT oncogene under control of the MMTV promoter were implanted in the mammary fat pads of these two groups of mice. Mice with Treg cells that lacked CCR8 displayed a significant reduction in the rate of primary tumor growth (FIG. 9A) as well as lung metastases (FIG. 9B). These data provide additional confirmation that, as described herein, CCR8 is an important means by which Treg cells can modulate anti-tumor immunity.

Figure 10:
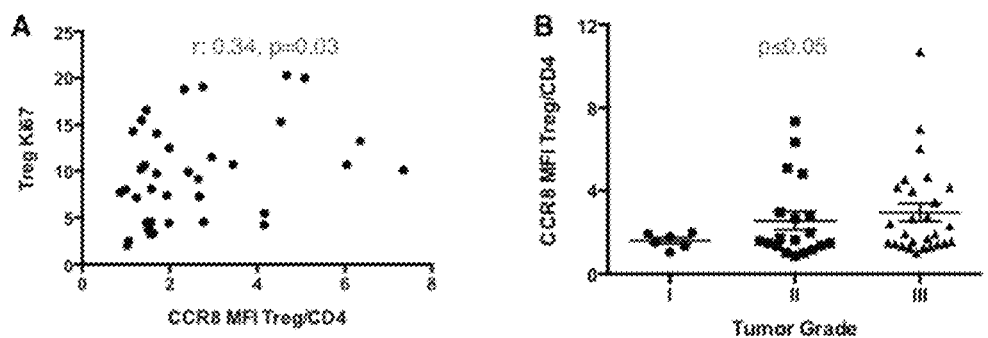
FIG. 10, Panels A-B.

We also analyzed tumor-infiltrating lymphocytes (TILs) of primary human breast carcinomas by flow cytometry. With IRB approval we isolated TILs from surgical specimens of patients undergoing surgery for primary breast cancer. The TILs were analyzed by flow cytometry to determine the phenotypic characteristics of the tumor-infiltrating Treg cells. These data were correlated to tumor grade as determined by the pathologic review of the tumor specimens. As can be seen, for example, with reference to FIG. 10A, there was a positive correlation between the expression of CCR8 on Treg cells and their proliferative state (FIG. 10A). This finding documents, as described herein, that CCR8 may play a role in the maintenance of Treg cells in the human tumor microenvironment.

We also compared relative expression of CCR8 on Treg cells infiltrating human breast cancer with tumor grade. As shown in FIG. 10B, increasing expression of CCR8 by tumor infiltrating Treg cells is associated with higher grade tumors (FIG. 10B).

These data further confirm, as demonstrated herein, that Treg cells are important mechanisms of immune tolerance to tumors. Additionally, these data further confirm that CCR8 expression by Treg cells contributes to their ability to thwart anti-tumor immune responses and represents a promising means by which human tumor infiltrating Treg cells can be targeted for the immunotherapy of cancer patients.

REFERENCES

1. Dunn G P, Old L J, Schreiber R D. The immunobiology of cancer immunosurveillance and immunoediting. Immunity 2004; 21(2):137-48.
2. Hodi F S, O'Day S J, McDermott D F, et al. Improved survival with ipilimumab in patients with metastatic melanoma. N Engl J Med 2010; 363(8):711-23.
3. Robert C, Thomas L, Bondarenko I, et al. Ipilimumab plus dacarbazine for previously untreated metastatic melanoma. N Engl J Med 2011; 364(26):2517-26.
4. Galluzzi L, Vacchelli E, Eggermont A, et al. Trial Watch: Adoptive cell transfer immunotherapy. Oncolmmunology 2012; 1(3):306-15.
5. Kantoff P W, Higano C S, Shore N D, et al. Sipuleucel-T immunotherapy for castration-resistant prostate cancer. N Engl J Med 2010; 363(5):411-22.
6. Josefowicz S Z, Niec R E, Kim H Y, et al. Extrathymically generated regulatory T cells control mucosal TH2 inflammation. Nature 2012; 482(7385):395-9.
7. Littman D R, Rudensky A Y. Th17 and regulatory T cells in mediating and restraining inflammation. Cell 2010; 140(6):845-58.
8. Samstein R M, Josefowicz S Z, Arvey A, et al. Extrathymic generation of regulatory T cells in placental mammals mitigates maternal-fetal conflict. Cell 2012; 150(1):29-38.
9. Bos P D, Plitas G, Rudra D, et al. Transient regulatory T cell ablation deters oncogene-driven breast cancer and enhances radiotherapy. J Exp Med 2013; 210(11):2435-66.
10. Savage P A, Malchow S, Leventhal D S. Basic principles of tumor-associated regulatory T cell biology. Trends Immunol 2012.
11. Galon J, Costes A, Sanchez-Cabo F, et al. Type, density, and location of immune cells within human colorectal tumors predict clinical outcome. Science 2006; 313 (5795):1960-4.
12. Sato E, Olson S H, Ahn J, et al. Intraepithelial CD8+ tumor-infiltrating lymphocytes and a high CD8+/regulatory T cell ratio are associated with favorable prognosis in ovarian cancer. Proc Natl Acad Sci USA 2005; 102(51): 18538-43.
13. Curiel T J, Coukos G, Zou L, et al. Specific recruitment of regulatory T cells in ovarian carcinoma fosters immune privilege and predicts reduced survival. Nat Med 2004; 10(9):942-9.
14. Zou W. Regulatory T cells, tumour immunity and immunotherapy. Nat Rev Immunol 2006; 6(4):295-307.
15. Zheng Y, Chaudhry A, Kas A, et al. Regulatory T-cell suppressor program co-opts transcription factor IRF4 to control T(H)2 responses. Nature 2009; 458(7236):351-6.
16. Koch M A, Tucker-Heard G, Perdue N R, et al. The transcription factor T-bet controls regulatory T cell homeostasis and function during type 1 inflammation. Nat Immunol 2009; 10(6):595-602.
17. Chaudhry A, Rudra D, Treuting P, et al. CD4+ regulatory T cells control TH17 responses in a Stat3-dependent manner. Science 2009; 326(5955):986-91.

18. Chaudhry A, Rudensky A Y. Control of inflammation by integration of environmental cues by regulatory T cells. J Clin Invest 2013; 123(3):939-44.
19. Josefowicz S Z, Lu L F, Rudensky A Y. Regulatory T cells: mechanisms of differentiation and function. Annu Rev Immunol 2012; 30:531-64.
20. Kim J M, Rasmussen J P, Rudensky A Y. Regulatory T cells prevent catastrophic autoimmunity throughout the lifespan of mice. Nat Immunol 2007; 8(2):191-7.
21. Pardoll D M. The blockade of immune checkpoints in cancer immunotherapy. Nat Rev Cancer 2012; 12(4):252-64.
22. Viguier, M., Lemaitre, F., Verola, O., Cho, M., Gorochov, G., Dubertret, L., Bachelez, H., Kourilsky, P., Ferradini, L. (2004). Foxp3 expressing CD4+CD25 high regulatory T cells are overrepresented in human metastatic melanoma lymph nodes an inhibit the function of infiltrating T cells. *Journal of Immunology*, 173: 1444-1453.
23. Bates, G. J., Fox, S. B., Han, C., Leek, R. D., Garcia, J. F., Harris, A. L., Banham, A. H. (2006). Quantification of regulatory T cells enables the identification of high-risk breast cancer patients and those at risk of late relapse. *Journal of Clinical Oncology*, 24(34): 5373-5380.
24. Mizukami, Y., Kono, K., Kawaguchi, Y., Akaike, H., Kamimura, K., Sugai, H., Fujii, H. (2008). Localisation pattern of Foxp3+ regulatory T cells is associated with clinical behaviour in gastric cancer. *British Journal of Cancer*, 98(1): 148-153.
25. Bohling, S. D., Allison, K. H. (2008). Immunoosuppressive regulatory T cells are associated with aggressive breast cancer phenotypes: a potential therapeutic target. *Modern Pathology*, 21: 1527-1532.
26. Wolf, D., Wolf, A. M., Rumpold, H., Fiegl, H., Zeimet, A. G., Muller-Holzner, E., Deibl, M., Gastl, G., Gunsilius, E., Marth, C. (2005). The expression of the regulatory T cell-specific forkhead box transcription factor foxp3 is associated with poor prognosis in ovarian cancer. *Clinical Cancer Research*, 11: 8326-8331.
27. Hiraoka, N., Onozato, K., Kosuge, T., Hirohashi, S. (2006). Prevalence of Foxp3+ regulatory T cells increases during the progression of pancreatic ductal adenocarcinoma and its premalignant lesions. Clinical Cancer Research, 12(18): 5423-5434.
28. Pages, F., Galon, J., Dieu-Nosjean, M. C., Tartour, E., Sautes-Fridman, C., Fridman, W-H. (2010). Immune infiltration in human tumors: a prognostic factor that should not be ignored. *Oncogene*, 29: 1093-1102.
29. Loi, S., Sirtaine, N., Piette, F., Salgado, R., Viale, G., Van Eenoo, F., Rouas, G., Francis, P., Crown, J. P. A., Hitre, E., deAzambuja, E., Quinaux, E., Di Leo, A., Michiels, S., Piccart, M. J., Sotiriou, C. (2013). Prognostic and Predictive Value of Tumor-Infiltrating Lymphocytes in a Phase III Randomized Adjuvant Breast Cancer Trial in Node-Positive Breast Cancer Comparing the Addition of Docetaxel to Doxorubicin With Doxorubicin-Based Chemotherapy: BIG 02-98. *Journal of Clinical Oncology*, 31(5): 860-867.
30. Prall, F., Duhrkop, T., Weirich, V., Ostwald, C., Lenz, P., Nizze, H., Barten, M. (2004). Prognostic role of CD8+ tumor-infiltrating lymphocytes in stage III colorectal cancer with and without microsatellite instability. *Human Pathology*, 35(7): 808-816.
31. Sharma, P., Wagner, K., Wolchok, J. D., Allison, J. P. (2011). Novel cancer immunotherapy agents with survival benefit: recent successes and next steps. *Nature Review Cancer*, 11: 805-812.
32. Ott, P. A., Hodi, F. S., Robert, C. (2013). CTLA-4 and PD-1/PD-L1 blockade: new immunotherapeutic modalities with durable clinical benefit in melanoma patients. *Clinical Cancer Resolution*, 19: 5300-5309.
33. Simpson, T. R., Li, F., Montalvo-Ortiz, W., Sepulveda, M. A., Bergerhoff, K., Arce, F., Roddie, C., Henry, J. Y., Yagita, H., Wolchok, J. D., Peggs, K. S., Ravetch, J. V., Allison, J. P., Quezada, S. A. (2013). Fc-dependent depletion of tumor-infiltrating regulatory T cells co-defines the efficacy of anti-CTLA-4 therapy against melanoma. *Journal of Experimental Medicine*, 210(9): 1695-1710.
34. Leach, D. R., Krummel, M. F., Allison, J. P. (1996). Enhancement of antitumor immunity by CTLA-4 blockade. *Science*, 271(5256): 1734-1736.
35. Scott, A. M., Wolchok, J. D., Old, L. J. (2012). Antibody therapy of cancer. *Nature Reviews Cancer*, 12: 278-287.
36. Fontenot, J. D., Gavin, M. A., Rudensky, A. Y. (2003). Foxp3 programs the development and function of CD4+ CD25+ regulatory T cells. *Nature*, 4(4): 330-336.
37. Yagi, H., Nomura, T., Nakamura, K., Yamazaki, S., Kitawaki, T., Hori, S., Maeda, M., Onodera, M, Uchiyama, T., Fujii, S., Sakaguchi, S. (2004). Crucial role of FOXP3 in the development and function of human CD25+CD4+ regulatory T cells. *International Immunology*, 16(11): 1643-1656.
38. Klages, K., Mayer, C. T., Lahl, K., Loddenkemper, C., Teng, M. W., Ngiow, M. W., Smyth, M. J., Hamann, A., Huehn, J., Sparwasser, T. (2010). Selective depletion of Foxp3+ regulatory T cells improves therapeutic vaccination against established melanoma. *Cancer Research*, 70(20): 7788-7799.
39. Teng, M. W., Ngiow, S. F., von Scheidt, B., McLaughlin, N., Sparwasser, T., Smyth, M. J. (2010). Conditional regulatory T-cell depletion releases adaptive immunity preventing carcinogenesis and suppressing established tumor growth. *Cancer Research*, 70(20):7800-7809.
40. Kim, J. M., Lahl, K., Hori, S., Loddenkemper, C., Chaudhry, A., deRoos, P., Rudensky, A., Sparwasser, T. (2009). Cutting edge: depletion of Foxp3+ cells leads to induction of autoimmunity by specific ablation of regulatory T cells in genetically targeted mice. *Journal of Immunology*, 182(12): 7631-7634.
41. Chinen, T., Volchkov, P. Y., Chervonsky, A. V., Rudensky, A. Y. (2010). A critical role for regulatory T cell-mediated control of inflammation in the absence of commensal bacteria. *Journal of Experimental Medicine*, 207 (11): 2323-2330.
42. Bindea, G., Mlecnik, B., Tosolini, M., Kirilovsky, A., Waldner, M., Obenauf, A. C., Angell, H., Fredrikson, T., Lafontaine, L., Berger, A., Bruneval, P., Fridman, W. H., Becker, C., Pages, F., Speicher, M. R., Trajanoski, Z., Galon, J. (2013). Spatiotemporal dynamics of intratumoral immune cells reveal the immune landscape in human cancer. *Immunity*, 39(4): 782-795.
43. Li, Y., Xie, X. (2013). A mixture model for expression deconvolution from RNA-seq in heterogeneous tissues. *BMC Bioinformatics*, 14(Suppl 5):S11.
44. Islam, S. A., Ling, M. F., Leung, J., Shreffler, W. G., Luster, A. D. (2013). Identification of human CCR8 as a CCL18 receptor. *Journal of Experimental Medicine*, 210 (10): 1889-1898.
45. Facciabene, A., Peng, X., Hagemann, I. S., Balint, K., Barchetti, A., Wang, L. P., Gimotty, P. A., Gilks, C. B., Lal, P., Zhang, L., Coukos, G. (2011). Tumor hypoxia promotes tolerance and angiogenesis via CCL28 and Treg cells. *Nature*, 475(7355): 226-230.

46. Hori, S., Nomura, T., Sakaguchi, S. (2003). Control of regulatory T cell development by the transcription factor Foxp3. *Science*, 299(5609): 1057-1061.
47. Bennett, C. L., Christie, J., Ramsdell, F., Brunkow, M. E., Ferguson, P. J., Whitesell, L., Kelly, T. E., Saulsbury, F. T., Chance, P. F., Ochs, H. D. (2001). The immune dysregulation, polyendocrinopathy, enteropathy, X-linked syndrome (IPEX) is caused by mutations of FOXP3. *Nature Genetics*, 27(1):20-21.
48. Williams, L. M. and Rudensky, A. Y. (2007). Maintenance of the Foxp3-dependent developmental program in mature regulatory T cells requires continued expression of Foxp3. *Nature Immunology*, 8(3): 277-284.
49. *Homo sapiens* ATCC® CRL-8294™
50. Shalem, O., Sanjana, N. E., Hartenian, E., Shi, X., Scott, D. A., Mikkelsen, T. S., Heckl, D., Ebert, B. L., Root, D. E., Doench, J. G., Zhang, F. (2014). Genome-scale CRISPR-Cas9 knockout screening in human cells. *Science*, 343(6166): 84-87.
51. Gavin, M. A., Rasmussen, J. P., Fontenot, J. D., Vasta, V., Manganiello, V. C., Beavo, J. A., Rudensky, A. Y. (2007). Foxp3-dependent programme of regulatory T-cell differentiation. *Nature*, 445: 771-775.
52. Yang, H., Wang, H., Shivalila, C. S., Cheng, A. W., Shi, L., Jaenisch, R. (2013). One-step generation of mice carrying reporter and conditional alleles by CRISPR/Cas-mediated genome editing. *Cell*, 154: 1370-1379.
53. Lal, G., Zhang, N., van der Touw, W., Ding, Y., Ju, W., Bottinger, E. P., Reid, S. P., Levy, D. E., Bromberg, J. S. (2009). Epigenetic regulation of Foxp3 expression in regulatory T cells by DNA methylation. *Journal of Immunology*, 182(1): 259-273.
54. Polansky, J. K., Kretschmer, K., Freyer, J., Floess, S., Garbe, A., Baron, U., Olek, S., Hamann, A., von Boehmer, H., Huehn, J. (2008). DNA methylation controls Foxp3 gene expression. *European Journal of Immunology*, 38: 1654-1663.
55. Wang, L., Liu, Y., Beier, U. H., Han, R., Bhatti, T. R., Akimova, T., Hancock, W. W. (2013). Foxp3+T-regulatory cells require DNA methyltransferase 1 expression to prevent development of lethal autoimmunity. *Blood*, 121: 3631-3639.
56. Schmidt, A. M., Zou, T., Joshi, R. P., Leichner, T. M., Pimentel, M. A., Sommers, C. L., Kambayashi, T. (2013). Diacylglycerol kinase z limits the generation of natural regulatory T cells. *Science Signaling*, 6(303): 101-111.
57. Buckner, J. H. (2010). Mechanisms of impaired regulation by CD4+CD25+FOXP+ regulatory T cells in human autoimmune diseases. *Nature Reviews Immunology*, 10: 849-859.
58. Fellman, C., Hoffman, T., Sridhar, V., Hopfgartner, B., Muhar, M., Roth, M., Lai, D. Y., Barbosa, I. A. M., Kwon, J. S., Guan, Y., Sinha, N., Zuber, J. (2013). An optimized microRNA backbone for effective single-copy RNAi. *Cell Reports*, 5(6): 1704-1713.
59. Mulligan A M, Raitman I, Feeley L, et al. Tumoral lymphocytic infiltration and expression of the chemokine CXCL10 in breast cancers from the Ontario Familial Breast Cancer Registry. Clinical cancer research: an official journal of the American Association for Cancer Research 2013; 19:336-46
60. Yan M, Jene N, Byrne D, et al. Recruitment of regulatory T cells is correlated with hypoxia-induced CXCR4 expression, and is associated with poor prognosis in basal-like breast cancers. Breast cancer research: BCR 2011; 13:R47
61. Deleeuw, et al. Clin. Cancer Res. 18, 3022, 2012)
62. T. Chinen, A. Y. Rudensky, The effects of commensal microbiota on immune cell subsets and inflammatory responses. *Immunological reviews* 245, 45 (January, 2012).
63. D. G. DeNardo et al., CD4(+) T cells regulate pulmonary metastasis of mammary carcinomas by enhancing protumor properties of macrophages. *Cancer cell* 16, 91 (Aug. 4, 2009).
64. L. V. Hooper, D. R. Littman, A. J. Macpherson, Interactions between the microbiota and the immune system. *Science* 336, 1268 (Jun. 8, 2012).
65. J. W. Verbsky, T. A. Chatila, Immune dysregulation, polyendocrinopathy, enteropathy, X-linked (IPEX) and IPEX-related disorders: an evolving web of heritable autoimmune diseases. *Current opinion in pediatrics* 25, 708 (December, 2013).
66. Y. P. Rubtsov et al., Regulatory T cell-derived interleukin-10 limits inflammation at environmental interfaces. *Immunity* 28, 546 (April, 2008).
67. M. Y. Gerner, W. Kastenmuller, I. Ifrim, J. Kabat, R. N. Germain, Histo-cytometry: a method for highly multiplex quantitative tissue imaging analysis applied to dendritic cell subset microanatomy in lymph nodes. *Immunity* 37, 364 (Aug. 24, 2012).
68. F. Barzaghi, L. Passerini, R. Bacchetta, Immune dysregulation, polyendocrinopathy, enteropathy, x-linked syndrome: a paradigm of immunodeficiency with autoimmunity. *Frontiers in immunology* 3, 211 (2012).
69. T. Ishida et al., Stevens-Johnson Syndrome associated with mogamulizumab treatment of adult T-cell leukemia/lymphoma. *Cancer Sci* 104, 647 (May, 2013).
70. H. Azukizawa, S. Sano, H. Kosaka, Y. Sumikawa, S. Itami, Prevention of toxic epidermal necrolysis by regulatory T cells. *European Journal of Immunology* 35, 1722 (June, 2005).
71. R. Takahashi et al., Defective regulatory T cells in patients with severe drug eruptions: timing of the dysfunction is associated with the pathological phenotype and outcome. *J Immunol* 182, 8071 (Jun. 15, 2009).
72. E. Antiga et al., Characterization of regulatory T cells in patients with dermatomyositis. *Journal of autoimmunity* 35, 342 (December, 2010).
73. Comprehensive molecular portraits of human breast tumours. *Nature* 490, 61 (Oct. 4, 2012).
74. C. M. Perou, Molecular stratification of triple-negative breast cancers. *The oncologist* 16 Suppl 1, 61 (2011).
75. E. A. Rakha, J. S. Reis-Filho, I. O. Ellis, Basal-like breast cancer: a critical review. *Journal of clinical oncology: official journal of the American Society of Clinical Oncology* 26, 2568 (May 20, 2008).
76. A. M. Mulligan et al., Tumoral lymphocytic infiltration and expression of the chemokine CXCL10 in breast cancers from the Ontario Familial Breast Cancer Registry. *Clinical cancer research: an official journal of the American Association for Cancer Research* 19, 336 (Jan. 15, 2013).
77. M. Yan et al., Recruitment of regulatory T cells is correlated with hypoxia-induced CXCR4 expression, and is associated with poor prognosis in basal-like breast cancers. *Breast cancer research: BCR* 13, R47 (2011).
78. D. M. Parkin, Global cancer statistics in the year 2000. *The lancet oncology* 2, 533 (September, 2001).
79. P. C. Enzinger, R. J. Mayer, Esophageal cancer. *The New England journal of medicine* 349, 2241 (Dec. 4, 2003).
80. A. Amedei, M. Benagiano, C. della Bella, E. Niccolai, M. M. D'Elios, Novel immunotherapeutic strategies of gastric cancer treatment. *Journal of biomedicine & biotechnology* 2011, 437348 (2011).
81. L. Shi et al., Efficacy of adjuvant immunotherapy with cytokine-induced killer cells in patients with locally advanced gastric cancer. *Cancer immunology, immunotherapy: CII* 61, 2251 (December, 2012).
82. S. Zhou et al., CCR7 Expression and Intratumoral FOXP3(+) Regulatory T Cells are Correlated with Overall Survival and Lymph Node Metastasis in Gastric Cancer. *PloS one* 8, e74430 (2013).
83. T. Sasada, M. Kimura, Y. Yoshida, M. Kanai, A. Takabayashi, CD4+CD25+ regulatory T cells in patients with gastrointestinal malignancies: possible involvement of regulatory T cells in disease progression. *Cancer* 98, 1089 (Sep. 1, 2003).
84. B. Deng et al., Intratumor hypoxia promotes immune tolerance by inducing regulatory T cells via TGF-beta1 in gastric cancer. *PloS one* 8, e63777 (2013).
85. K. Cetin, D. S. Ettinger, Y. J. Hei, C. D. O'Malley, Survival by histologic subtype in stage IV nonsmall cell lung cancer based on data from the Surveillance, Epidemiology and End Results Program. *Clinical epidemiology* 3, 139 (2011).
86. L. V. Kalialis, K. T. Drzewiecki, H. Klyver, Spontaneous regression of metastases from melanoma: review of the literature. *Melanoma research* 19, 275 (October, 2009).
87. A. Shablak et al., High-dose interleukin-2 can produce a high rate of response and durable remissions in appropriately selected patients with metastatic renal cancer. *J Immunother* 34, 107 (January, 2011).
88. K. I. Al-Shibli et al., Prognostic effect of epithelial and stromal lymphocyte infiltration in non-small cell lung cancer. *Clinical cancer research: an official journal of the American Association for Cancer Research* 14, 5220 (Aug. 15, 2008).
89. K. Shimizu et al., Tumor-infiltrating Foxp3+ regulatory T cells are correlated with cyclooxygenase-2 expression and are associated with recurrence in resected non-small cell lung cancer. *Journal of thoracic oncology: official publication of the International Association for the Study of Lung Cancer* 5, 585 (May, 2010).
90. R. P. Petersen et al., Tumor infiltrating Foxp3+ regulatory T-cells are associated with recurrence in pathologic stage I NSCLC patients. *Cancer* 107, 2866 (Dec. 15, 2006).
91. K. Suzuki et al., Clinical impact of immune microenvironment in stage I lung adenocarcinoma: tumor interleukin-12 receptor beta2 (IL-12Rbeta2), IL-7R, and stromal FoxP3/CD3 ratio are independent predictors of recurrence. *Journal of clinical oncology: official journal of the American Society of Clinical Oncology* 31, 490 (Feb. 1, 2013).
92. Y. Q. He et al., FoxP3 genetic variants and risk of non-small cell lung cancer in the Chinese Han population. *Gene* 531, 422 (Dec. 1, 2013).
93. J. R. Brahmer et al., Safety and activity of anti-PD-L1 antibody in patients with advanced cancer. *The New England journal of medicine* 366, 2455 (Jun. 28, 2012).
94. S. L. Topalian et al., Safety, activity, and immune correlates of anti-PD-1 antibody in cancer. *The New England journal of medicine* 366, 2443 (Jun. 28, 2012).
95. Nat Immunol. 2011 February; 12(2):167-77. doi: 10.1038/ni.1984. Epub 2011 Jan. 9.
96. Biochem Pharmacol. 2012 Mar. 15; 83(6):778-87. doi: 10.1016/j.bcp.2011.12.021. Epub 2011 Dec. 24.
97. Adv Immunol. 2006; 90:83-131.
98. Deleeuw, et al. Clin. Cancer Res. 18, 3022, 2012

What is claimed is:

1. A method of treating cancer by administering to a cancer patient who has a tumor in which CCR8 on tumor-infiltrating Treg cells is overexpressed relative to its level on circulating blood Treg cells, an antibody agent comprising CDRs of an antibody that binds specifically to CCR8 so that the antibody agent binds specifically to CCR8 and tumor-infiltrating Treg cells are specifically depleted in the subject, to a greater extent than are normal-tissue infiltrating T-cells.

2. The method of claim 1, wherein the CCR8-targeting antibody agent comprises a payload moiety that, when delivered to tumor-infiltrating Treg cells, depletes such cells from the tumor.

3. The method of claim 1, which method further comprises targeting CCR4.

4. The method of claim 3, wherein targeting CCR4 comprises administering to the subject a composition comprising a CCR4-targeting antibody agent.

5. The method of claim 4, wherein the CCR4-targeting antibody agent is or comprises a bifunctional antibody agent that targets both CCR8 and CCR4.

6. The method of claim 1, further comprising administering one or more immunomodulatory therapeutic modalities to the subject.

* * * * *